(12) United States Patent
Fukuda et al.

(10) Patent No.: US 7,754,757 B2
(45) Date of Patent: Jul. 13, 2010

(54) BICYCLOESTER DERIVATIVE

(75) Inventors: Yasumichi Fukuda, Tochigi (JP); Yoshikazu Asahina, Tochigi (JP); Kohei Ohata, Tochigi (JP); Kazuya Yokota, Tochigi (JP); Koji Murakami, Tochigi (JP); Toshiyuki Matsui, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 792 days.

(21) Appl. No.: 10/588,660

(22) PCT Filed: Feb. 1, 2005

(86) PCT No.: PCT/JP2005/001377

§ 371 (c)(1),
(2), (4) Date: Sep. 1, 2006

(87) PCT Pub. No.: WO2005/075421

PCT Pub. Date: Aug. 18, 2005

(65) Prior Publication Data

US 2008/0146818 A1  Jun. 19, 2008

(30) Foreign Application Priority Data

Feb. 5, 2004  (JP)  ............... 2004-029856

(51) Int. Cl.
*A61K 31/40* (2006.01)
*C07D 207/04* (2006.01)
(52) U.S. Cl. .............. 514/423; 548/530; 548/540; 514/408
(58) Field of Classification Search ........... 548/530, 548/540; 514/408, 423
See application file for complete search history.

(56) References Cited

U.S. PATENT DOCUMENTS

| | | | |
|---|---|---|---|
| 5,939,560 A | 8/1999 | Jenkins et al. | |
| 5,965,764 A | 10/1999 | Matsuoka et al. | |
| 6,166,063 A | 12/2000 | Villhauer | |
| 6,201,132 B1 | 3/2001 | Jenkins et al. | |
| 6,303,661 B1 | 10/2001 | Demuth et al. | |
| 6,432,969 B1 | 8/2002 | Villhauer | |
| 6,849,622 B2 | 2/2005 | Yasuda et al. | |
| 7,138,397 B2 * | 11/2006 | Yasuda et al. | 514/254.01 |
| 7,332,487 B2 * | 2/2008 | Yasuda et al. | 514/235.5 |
| 7,514,571 B2 | 4/2009 | Fukuda et al. | |
| 7,560,569 B2 | 7/2009 | Fukuda et al. | |
| 2001/0025023 A1 | 9/2001 | Carr | |
| 2001/0031780 A1 | 10/2001 | Kanstrup et al. | |
| 2002/0006899 A1 | 1/2002 | Pospisilik et al. | |
| 2002/0019411 A1 | 2/2002 | Robl et al. | |
| 2002/0037829 A1 | 3/2002 | Aronson et al. | |
| 2002/0049190 A1 | 4/2002 | Bridger et al. | |
| 2002/0103384 A1 | 8/2002 | Kanstrup et al. | |
| 2002/0110560 A1 | 8/2002 | Demuth et al. | |
| 2002/0193390 A1 | 12/2002 | Villhauer | |
| 2003/0100563 A1 | 5/2003 | Edmondson et al. | |
| 2003/0105077 A1 | 6/2003 | Kanstrup et al. | |
| 2003/0176357 A1 | 9/2003 | Pospisilik et al. | |
| 2003/0225102 A1 | 12/2003 | Sankaranarayanan | |
| 2004/0063935 A1 | 4/2004 | Yasuda et al. | |
| 2004/0072892 A1 | 4/2004 | Fukushima et al. | |
| 2004/0082607 A1 | 4/2004 | Oi et al. | |
| 2004/0106655 A1 | 6/2004 | Kitajima et al. | |
| 2004/0106802 A1 | 6/2004 | Sankaranarayanan | |
| 2004/0121964 A1 | 6/2004 | Madar et al. | |
| 2004/0152745 A1 | 8/2004 | Jackson et al. | |
| 2004/0167133 A1 | 8/2004 | Edmondson et al. | |
| 2004/0167341 A1 | 8/2004 | Haffner et al. | |
| 2004/0171848 A1 | 9/2004 | Haffner et al. | |
| 2004/0176428 A1 | 9/2004 | Edmondson et al. | |
| 2004/0229926 A1 | 11/2004 | Yasuda et al. | |
| 2004/0242636 A1 | 12/2004 | Haffner et al. | |
| 2005/0054678 A1 | 3/2005 | Yasuda et al. | |
| 2005/0070719 A1 | 3/2005 | Belyakov et al. | |
| 2005/0130981 A1 | 6/2005 | Aranyl et al. | |
| 2005/0148606 A1 | 7/2005 | Kanstrup et al. | |
| 2005/0153973 A1 | 7/2005 | Aranyl et al. | |
| 2005/0164989 A1 | 7/2005 | Abe et al. | |
| 2005/0176771 A1 | 8/2005 | Hayakawa et al. | |
| 2005/0245538 A1 | 11/2005 | Kitajima et al. | |

(Continued)

FOREIGN PATENT DOCUMENTS

JP   2002-356471   12/2002

(Continued)

OTHER PUBLICATIONS

Deacon et al., "Glucagon-like peptide I undergoes differential tissue-specific metabolism in the anesthetized pig", American Journal of Physiology, v271, pp. E458-E464 (1996).

(Continued)

*Primary Examiner*—Golam M Shameem
(74) *Attorney, Agent, or Firm*—Wenderoth, Lind & Ponack, LLP.

(57) ABSTRACT

Novel bicycloester derivatives and pharmaceutically acceptable salts thereof have high DPP-IV inhibitory activity.

The novel bicycloester derivatives are represented by the general formula (1):

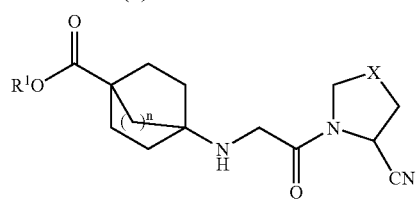

(1)

Pharmaceutically acceptable salts thereof are also included (Example: (2S,4S)-1-[[N-(4-ethoxycarbonylbicyclo[2.2.2]oct-1-yl)amino]acetyl]-4-fluoropyrrolidine-2-carbonitrile)).

8 Claims, 1 Drawing Sheet

U.S. PATENT DOCUMENTS

| | | | |
|---|---|---|---|
| 2005/0266080 | A1 | 12/2005 | Desai et al. |
| 2006/0142585 | A1 | 6/2006 | Thomas et al. |
| 2006/0173056 | A1 | 8/2006 | Kitajima et al. |
| 2006/0210627 | A1 | 9/2006 | Pfeffer et al. |
| 2006/0241146 | A1 | 10/2006 | Yasuda et al. |
| 2006/0270679 | A1 | 11/2006 | Edmondson et al. |
| 2007/0112059 | A1 | 5/2007 | Fukushima et al. |
| 2007/0112205 | A1 | 5/2007 | Fukushima et al. |
| 2007/0167501 | A1 | 7/2007 | Fukuda et al. |
| 2007/0265320 | A1 | 11/2007 | Fukuda et al. |
| 2008/0038341 | A1 | 2/2008 | Kowalski et al. |
| 2008/0050443 | A1 | 2/2008 | Kowalski et al. |
| 2009/0048454 | A1 | 2/2009 | Asahina et al. |

FOREIGN PATENT DOCUMENTS

| | | |
|---|---|---|
| JP | 2002-356472 | 12/2002 |
| JP | 2003-520849 | 7/2003 |
| JP | 2004-2367 | 1/2004 |
| JP | 2004-2368 | 1/2004 |
| JP | 2004-26820 | 1/2004 |
| JP | 2004-503531 | 2/2004 |
| JP | 2006-160733 | 6/2006 |
| JP | 2008/239543 | 10/2008 |
| JP | 2008/290969 | 12/2008 |
| JP | 2009/114127 | 5/2009 |
| WO | 95/15309 | 6/1995 |
| WO | 98/19998 | 5/1998 |
| WO | 01/34594 | 5/2001 |
| WO | 01/55105 | 8/2001 |
| WO | 01/68603 | 9/2001 |
| WO | 02/07446 | 1/2002 |
| WO | 03/002553 | 1/2003 |
| WO | 03/004496 | 1/2003 |
| WO | 03/015775 | 2/2003 |
| WO | 03/017936 | 3/2003 |
| WO | 03/57144 | 7/2003 |
| WO | 03/057666 | 7/2003 |
| WO | 03/074500 | 9/2003 |
| WO | 03/080633 | 10/2003 |
| WO | 03/084940 | 10/2003 |
| WO | 03/095425 | 11/2003 |
| WO | 03/106456 | 12/2003 |
| WO | WO2004/000776 | 12/2003 |
| WO | 2004/007446 | 1/2004 |
| WO | 2004/026822 | 4/2004 |
| WO | 2004/099185 | 11/2004 |
| WO | 2005/067976 | 7/2005 |
| WO | 2005/117841 | 12/2005 |
| WO | 2006/021455 | 3/2006 |
| WO | 2006/040625 | 4/2006 |
| WO | 2006/043595 | 4/2006 |
| WO | 2006/078593 | 7/2006 |
| WO | 2006/135723 | 12/2006 |
| WO | 2007/102286 | 9/2007 |
| WO | 2008/096841 | 8/2008 |
| WO | 2008/114857 | 9/2008 |

OTHER PUBLICATIONS

Knudsen et al., "Glucagon-like peptide-1-(9-36) amide is a major metabolite of glucagon-like peptide-1-(7-36) amide after in vivo administration dogs, and it acts as an antagonist on the pancreatic receptor", European Journal of Pharmacology, vol. 318, pp. 429-435 (1996).

Siegel et al., "Comparison of the effect of GIP and GLP-I (7-36amide) on insulin release from rat pancreatic islets", European Journal Clinical Investigation, v22, p. 154-157 (1992).

Kreymann et al., "Glucagon-like Peptide-I-7-36: A Physiological Incretin in Man", Lancet, v2, p1300-1301 (1987).

Fehmann et al., "Insulinotropic Hormone Glucagon-like Peptide-I(7-37) Stimulation of Proinsulin Gene Expression and Proinsulin Biosynthesis in Insulinoma BTC-I Cells", Endocrinology, v130, p. 159-166 (1992).

Buteau et al., "Glucagon-like peptide-1-promotes DNA Synthesis, activates phosphyatidylinositol 3-kinase and increase transcription factor pancreatic and duodenal homeobox gene 1 (PDX-I) DNA binding activity in beta (INS-1)-cells", Diabetologia, v42, p. 856-864 (1999).

Egan, et al., "Glucagon-Like Peptide-1(7-36)Amide (GLP-1) Enhances Insulin-Stimulated Glucose Metabolism in 3T3-L1 Adipocytes: One of Several Potential Extrapancreatic Sites of GLP-1 Action", Endocrinology, v135, p. 2070-2075 (1994).

Villanueva-Penacarrillo, et al., "Potent glycogenic effect of GLO-1(7-36)amide in rat skeletal muscle", Diabetologia, v37, p. 1163 (1994).

Efendic, et al., "Glucagon-like Insulinotropic Peptide Has a Stronger Antidiabetogenic Effect than Glibenclamide", Digestion, v54, p. 392-393 (1993).

Anvari et al., "Effects of GLP-1 on Gastric Emptying, Antropyloric Motility, and Transpyloric Flow in Response to a Nonnutrient Liquid", Dig. Dis. Sci, v43, p. 1133-1140 (1998).

Holst et al., "Inhibition of the Activity of Dipeptidyl-Peptidase IV as a Treatment for Type 2 Diabetes", Diabetes, v47, pp. 1663-1670 (1998).

Balkan et al., "Inhibition of dipeptidyl peptidase IV with NVP-DPP728 increase plasma GLP-1 (7-36 amide) concentrations and improves oral glucose tolerance in obese Zucker rats", Diabetologia, v42, pp. 1324-1331(1999).

Blazquez et al., "Selective Decrease of CD26 Expression in T Cells From HIV-1-Infected Individuals", Journal of Immunology, v149, p. 3073-3077 (1992).

Subramanyam et al., "Mechanism of HIV-1 Tat Induced Inhibition of Antigen-Specific T Cell Responsiveness", Journal of Immunology, v150, p. 2544-2553 (1993).

Schon et al., "Dipeptidyl Peptidase IV in the Immune System", Biological Chemistry Hpppe-Seyler, p. 305-311 (1991).

Mattern et al., "Expression of CD26 (Dipeptidyl Peptidase IV) on Resting and Activated Human T-Lymphocytes", Scandinavian Journal of Immunology, v33, p. 737-748 (1991).

Schon et al., "Dipeptidyl Peptidase IV in Human T Lymphocytes", Scandinavian Journal of Immunology, v29, p. 127-132 (1989).

Kameoka et al., Direct Association of Adenosine Deaminase with T Cell Activation Antigen Science, v261, p. 466-469 (1993).

Raynaud, et al., "Characterization of Specific Proteases Associated with the Surface of Human Skin Fibroblasts, and Their Modulation in Pathology", Journal of Cellular Physiology, v151, p. 378-385 (1992).

Vanhoof et al., "Distribution of Proline-Specific Aminopeptidases in Human Tissues and Body Fluids", European Journal of Clinical Chemistry and Clinical Biochemistry, v30, p. 333-338 (1992).

Johnson et al., "Lung Endothelial Dipeptidyl Peptidase IV Is an Adhesion Molecule for Lung-metastatic Rat Breast and Prostate Carcinoma Cells", Journal of Cell Biology, v121, p. 1423-1432 (1993).

Villhauer et al., "1-[[-Hydroxy-a-adamantyl)amino[acety1]-2-cyano-(S)-pyrrolidine", Journal ofMedicinal Chemistry, v46, p. 2774-2789, 2003.

Fukushima et al., "Synthesis and structure-activity relationships of potent 3-or 4-substitued-2-cyanopyrrolidine dipeptidyl peptidase IV inhibitors", Bioorganic & Medicinal Chemistry, v12, p. 6053-6061, 2004.

Della et al., "Synthesis of Bridgehead-Bridgehead Substituted Bicycloalkanes", Australian J. Chem. (1985), 38(11), 1705-1718.

Grob et al., "283. Die Synthese von-4-substituierten", Helv. Chim. Acta., (1979), 62, 2802-2816.

Asghari et al., "Enamine Chemistry", J. Chem. Soc. Prekin I, (1979), 2180-2183.

Morita et al., "A Novel Cyclization of 4-acetyl-1-methoxy-1-cyclohexene to 4-Alkoxybicyclo[2.2.2]octan-2-ones", J. Org. Chem., (1966), 31, 229-232.

Seebacher et al., "Structural Requirements for the Antiprotozoal Activity of 4-aminobicyclo[2.2.2]octan-2-ols", Montshefte fuer Chemie, (2006), 137, 471-482.

Roberts et al., "Syntheses of Some 4-Substitued Bicyclo [2.2.2]octane-1-carboxylic acid", J. Am. Chem. Soc., (1953), 75, 637-641.

* cited by examiner

BICYCLOESTER DERIVATIVE

TECHNICAL FIELD

The present invention relates to bicycloester derivatives and pharmaceutically acceptable salts thereof that have dipeptidylpeptidase IV (DPP-IV) inhibitory activity and are useful in the prevention and/or treatment of type II diabetes and other diseases that involve DPP-IV.

BACKGROUND ART

Dipeptidylpeptidase IV (EC3.4.14.5, referred to as "DPP-IV" or "CD26," hereinafter) is a serine protease that specifically hydrolyzes polypeptides having proline or alanine at position 2 on the C-terminal side of these amino acid residues, cleaving dipeptides Xaa-Pro or Xaa-Ala from the N-terminus of the polypeptides (Xaa may be any amino acid).

One biological function of DPP-IV is the inactivation of glucagon-like peptide 1 (GLP-1) by hydrolyzing the N-terminal His-Ala dipeptide of GLP-1 (Non-Patent Document 1). The GLP-1 inactivated by DPP-IV is thought to act as an antagonist on GLP-1 receptors, further decreasing the physiological activity of GLP-1 (Non-Patent Document 2). GLP-1, a peptide hormone secreted from endocrine L-cells found primarily in intestinal epithelium, is known to act on β-cells of the pancreatic Langerhans' islets in a glucose level-dependent manner to promote the insulin secretion, thus decreasing the blood glucose level (Non-Patent Documents No. 3 and 4). Having an ability to promote insulin biosynthesis and β-cell growth, GLP-1 is an essential factor for the maintenance of β-cells (Non-Patent Documents 5 and 6). It has been reported that GLP-1 also acts to promote glucose utilization by peripheral tissue and, when intraventricularly administered, decreases food intake and motility of GI tract (Non-Patent Documents 7 through 10).

A DPP-IV inhibitor is believed to increase the GLP-1 activity by suppressing the decomposition of innate GLP-1. The increased GLP-1 activity stimulates insulin secretion and improves glucose metabolism. For this reason, DPP-IV inhibitors are expected to be useful agents in the prevention and/or treatment of diabetes, in particular type II diabetes (Non-Patent Documents 11 and 12). The compounds are expected to be also effective in the prevention and/or treatment of other diseases that are caused or worsened by decreased glucose metabolism (for example, diabetic complications, hyperinsulinemia, hyperglycemia, abnormal lipid metabolism, and obesity).

The roles of DPP-IV in a living body other than the inactivation of GLP-1 and how the enzyme is involved in the onset of various diseases have been described in many reports as described below.

(a) DPP-IV inhibitors and their antibodies prevent the invasion of HIV into cells. Expression of CD26 is reduced in T-cells derived from patients infected with HIV-1 (Non-Patent Document 13). HIV-1 Tat protein binds to DPP-IV (Non-Patent Document 14).

(b) DPP-IV is involved in immune responses. DPP-IV inhibitors and their antibodies suppress the growth of T-cells stimulated by antigens (Non-Patent Document 15). T-cells stimulated by antigens express an increased level of DPP-IV (Non-Patent Document 16). DPP-IV is involved in the cytokine production and other functions of T-cells (Non-Patent Document 17). DPP-IV binds to adenosine deaminase (ADA) on the T-cell surface (Non-Patent Document 18).

(c) Expression of DPP-IV is increased in the skin fibroblasts of patients with rheumatoid arthritis, psoriasis, and lichen planus (Non-Patent Document 19).

(d) High DPP-IV activity is observed in patients with benign prostatic hypertrophy and in the homogenate of the prostatic tissue (Non-Patent Document 20). DPP-IV in the lung endothelium acts as an adhesive molecule for lung-metastatic breast cancer and prostatic cancer in rats (Non-Patent Document 21).

(e) The DPP-IV defective variant of F344 rats has lower blood pressure than the wild-type F344 rats. DPP-IV interacts with a protein that plays a crucial role in sodium reabsorption by the kidney (Patent Documents 1 and 2).

(f) The inhibition of DPP-IV activity offers an effective approach to the prevention and/or treatment of myelosuppressive diseases, while DPP-IV-activating agents are expected to serve as drugs to increase the white blood cell count and/or treat infectious diseases (Patent Document 3).

These observations indicate that DPP-IV inhibitors can be useful agents in the prevention and/or treatment of diabetes (in particular, type II diabetes) and/or diseases other than diabetic complications that involve DPP-IV. For example, DPP-IV inhibitors are expected to be useful in the prevention and/or treatment of AIDS following infection with HIV-1, rejection following organ/tissue transplantation, multiple sclerosis, rheumatoid arthritis, inflammation, allergies, osteoporosis, psoriasis and lichen planus, benign prostatic hypertrophy, lung metastasis of breast and prostatic cancers, hypertension and infectious diseases. DPP-IV inhibitors are also expected to be used to facilitate diuresis, decrease myelosuppression and increase white blood cell count.

Among existing DPP-IV inhibitors are pyrrolidine derivatives described in Patent Documents 4 through 11, heterocyclic derivatives described in Patent Documents 12 and 13, and β-amino acid derivatives described in Patent Documents 14 and 15.

Patent Document 16, a US patent, discloses a single bicycle [2.2.2]octane derivative that has DPP-IV inhibitory activity. This compound, however, is completely different from the compounds of the present invention in its structure and mechanism for DPP-IV inhibition. Patent Document 17 mentions a bicycle derivative structurally similar to the compounds of the present invention. However, there is no description in this literature concerning any of the compounds of the present invention, nor have any examples been presented of the compounds.

None of the previously described DPP-IV inhibitors are practical enough in terms of DPP-IV inhibitory activity, selectivity for DPP-IV, stability, toxicity and biological kinetics. Thus, a constant need exists for effective DPP-IV inhibitors.

[Non-Patent Document 1] American Journal of Physiology, Vol. 271 (1996): ppE 458-E464.
[Non-Patent Document 2] European Journal of Pharmacology, Vol. 318 (1996): pp 429-435.
[Non-Patent Document 3] European Journal Clinical Investigation, Vol. 22 (1992): p 154.
[Non-Patent Document 4] Lancet, Vol. 2 (1987): p 1300.
[Non-Patent Document 5] Endocrinology, Vol. 130 (1992): p 159.
[Non-Patent Document 6] Diabetologia, Vol. 42 (1999):p 856.
[Non-Patent Document 7] Endocrinology, Vol. 135 (1994): p 2070.
[Non-Patent Document 8] Diabetologia, Vol. 37 (1994): p 1163.
[Non-Patent Document 9] Digestion, Vol. 54 (1993): p 392.

[Non-Patent Document 10] Dig. Dis. Sci., Vol. 43 (1998): p 1133.
[Non-Patent Document 11] Diabetes, Vol. 47 (1998): pp 1663-1670.
[Non-Patent Document 12] Diabetologia, Vol. 42 (1999): pp 1324-1331.
[Non-Patent Document 13] Journal of Immunology, Vol. 149 (1992): p 3037.
[Non-Patent Document 14] Journal of Immunology, Vol. 150 (1993): p 2544.
[Non-Patent Document 15] Biological Chemistry Hpppe-Seyler (1991): p 305.
[Non-Patent Document 16] Scandinavian Journal of Immunology, Vol. 33 (1991): p 737.
[Non-Patent Document 17] Scandinavian Journal of Immunology, Vol. 29 (1989): p 127.
[Non-Patent Document 18] Science, Vol. 261 (1993): p 466.
[Non-Patent Document 19] Journal of Cellular Physiology, Vol. 151 (1992): p 378.
[Non-Patent Document 20] European Journal of Clinical Chemistry and Clinical Biochemistry, Vol. 30 (1992): p 333.
[Non-Patent Document 21] Journal of Cell Biology, Vol. 121 (1993): p 1423.
[Patent Document 1] WO 03/015775 Pamphlet
[Patent Document 2] WO 03/017936 Pamphlet
[Patent Document 3] WO 03/080633 Pamphlet
[Patent Document 4] WO 95/15309 Pamphlet
[Patent Document 5] WO 98/19998 Pamphlet
[Patent Document 6] WO 00/34241 Pamphlet
[Patent Document 7] WO 02/14271 Pamphlet
[Patent Document 8] WO 02/30890 Pamphlet
[Patent Document 9] WO 02/38541 Pamphlet
[Patent Document 10] WO 03/002553 Pamphlet
[Patent Document 11] US 02/0193390 Publication
[Patent Document 12] WO 02/062764 Pamphlet
[Patent Document 13] WO 03/004496 Pamphlet
[Patent Document 14] WO 03/000180 Pamphlet
[Patent Document 15] WO 03/004498 Pamphlet
[Patent Document 16] US 02/0193390 Publication
[Patent Document 17] WO 02/38541 Pamphlet

DISCLOSURE OF THE INVENTION

Problems to be Solved by the Invention

It is an object of the present invention to provide a novel compound that has high DPP-IV inhibitory activity, as well as pharmaceutically acceptable salts thereof. It is another object of the present invention to provide a pharmaceutical composition containing the novel compound that has high DPP-IV inhibitory activity or a pharmaceutically acceptable salt thereof. It is still another object of the present invention to provide a prophylactic and/or therapeutic agent for diabetes and associated complications, as well as a prophylactic and/or therapeutic agent for diseases involving DPP-IV.

Means to Solve the Problems

According to the present invention, there are provided a novel bicycloester derivative that has high DPP-IV inhibitory activity, and pharmaceutically acceptable salts thereof. Also provided is a pharmaceutical composition containing the novel bicycloester derivative that has high DPP-IV inhibitory activity, or a pharmaceutically acceptable salt thereof. Further provided are a prophylactic and/or therapeutic agent for diabetes and associated complications, and a prophylactic and/or therapeutic agent for diseases involving DPP-IV.

Thus, the present invention concerns the following:
1) A bicycloester derivative represented by the following general formula (1):

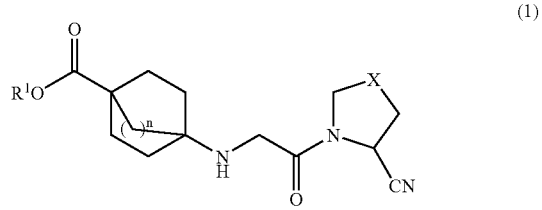

[wherein $R^1$ is a substituted or unsubstituted $C_1$ to $C_6$ alkyl group, substituted or unsubstituted $C_3$ to $C_6$ cycloalkyl group, tetrahydropyranyl group, substituted or unsubstituted arylmethyl group, substituted or unsubstituted arylethyl group, substituted or unsubstituted aromatic hydrocarbon group, substituted or unsubstituted aromatic heterocyclic ring, or substituted or unsubstituted aliphatic heterocyclic ring; X is $CH_2$, CHF, $CF_2$, CHOH, S, or O; and n is 1, 2, or 3.], or a pharmaceutically acceptable salt thereof.

2) An intermediate in the production of the bicycloester derivative of 1) above, represented by the following general formula (2):

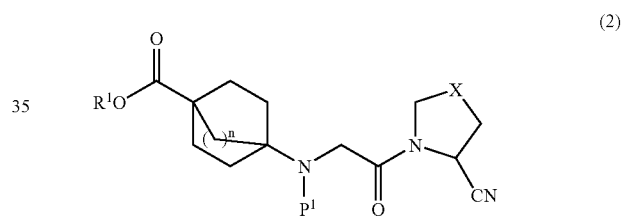

[wherein $R^1$ is a substituted or unsubstituted $C_1$ to $C_6$ alkyl group, substituted or unsubstituted $C_3$ to $C_6$ cycloalkyl group, tetrahydropyranyl group, substituted or unsubstituted arylmethyl group, substituted or unsubstituted arylethyl group, substituted or unsubstituted aromatic hydrocarbon group, substituted or unsubstituted aromatic heterocyclic ring, or substituted or unsubstituted aliphatic heterocyclic ring; X is $CH_2$, CHF, $CF_2$, CHOH, S, or O; n is 1, 2, or 3; and $P^1$ is a protective group for an amino group.].

3) A pharmaceutical product containing as an active ingredient the bicycloester derivative of 1) above or a pharmaceutically acceptable salt thereof.

4) A DPP-IV inhibitor containing as an active ingredient the bicycloester derivative of 1) above or a pharmaceutically acceptable salt thereof.

5) A therapeutic agent for a disease involving DPP-IV containing as an active ingredient the bicycloester derivative of 1) above or a pharmaceutically acceptable salt thereof.

6) The therapeutic agent according to 5) above, wherein the disease involving DPP-IV is diabetes or an associated complication.

The term "substituted or unsubstituted $C_1$ to $C_6$ alkyl group" as used herein refers to a $C_1$ to $C_6$ alkyl group (such as methyl group, cyclopropylmethyl group, ethyl group, propyl group, 1-methylethyl group, 1-methylpropyl group, 2-methylpropyl group, 1-ethylpropyl group, 2-ethylpropyl group, butyl group, t-butyl group, and hexyl group) that may have 1 to 5 substituents selected from halogen atom, hydroxy group, cyano group, $C_1$ to $C_6$ alkoxy group, substituted or unsubstituted aryloxy group, $C_1$ to $C_6$ alkylcarbonyl group, $C_1$ to $C_6$ alkoxycarbonyl group, $C_1$ to $C_6$ alkylthio group, amino group, mono- or di-substituted $C_1$ to $C_6$ alkylamino group, 4- to 9-membered cyclic amino group that may contain 1 to 3 heteroatoms, formylamino group, $C_1$ to $C_6$ alkylcarbonylamino group, $C_1$ to $C_6$ alkoxycarbonylamino group, $C_1$ to $C_6$ alkylsulfonylamino group, and substituted or unsubstituted arylsulfonylamino group.

The term "substituted or unsubstituted $C_3$ to $C_6$ cycloalkyl group" refers to a $C_3$ to $C_6$ cycloalkyl group (such as cyclopropyl group, cyclobutyl group, cyclopentyl group, and cyclohexyl group) that may have 1 to 5 substituents selected from halogen atom, hydroxy group, cyano group, $C_1$ to $C_6$ alkoxy group, substituted or unsubstituted aryloxy group, $C_1$ to $C_6$ alkylcarbonyl group, $C_1$ to $C_6$ alkoxycarbonyl group, $C_1$ to $C_6$ alkylthio group, amino group, mono- or di-substituted $C_1$ to $C_6$ alkylamino group, 4- to 9-membered cyclic amino group that may contain 1 to 3 heteroatoms, formylamino group, $C_1$ to $C_6$ alkylcarbonylamino group, $C_1$ to $C_6$ alkoxycarbonylamino group, $C_1$ to $C_6$ alkylsulfonylamino group, and substituted or unsubstituted arylsulfonylamino group.

The term "substituted or unsubstituted arylmethyl group" refers to an arylmethyl group (such as phenylmethyl group, naphthylmethyl group, pyridylmethyl group, quinolylmethyl group, and indolylmethyl group) that may have 1 to 5 substituents selected from halogen atom, substituted or unsubstituted $C_1$ to $C_6$ alkyl group, hydroxy group, cyano group, nitro group, substituted or unsubstituted $C_1$ to $C_6$ alkoxy group, substituted or unsubstituted aryloxy group, $C_1$ to $C_6$ alkylcarbonyl group, $C_1$ to $C_6$ alkoxycarbonyl group, $C_1$ to $C_6$ alkylthio group, amino group, mono- or di-substituted or unsubstituted $C_1$ to $C_6$ alkylamino group, substituted or unsubstituted arylamino group, 4- to 9-membered cyclic amino group that may contain 1 to 3 heteroatoms, formylamino group, $C_1$ to $C_6$ alkylcarbonylamino group, $C_1$ to $C_6$ alkoxycarbonylamino group, $C_1$ to $C_6$ alkylsulfonylamino group, and substituted or unsubstituted arylsulfonylamino group.

The term "substituted or unsubstituted ethyl group" refers to an arylethyl group (such as 1-phenethyl group, 2-phenethyl group, 1-naphthylethyl group, and 2-naphthylethyl group) that may have 1 to 5 substituents selected from halogen atom, substituted or unsubstituted $C_1$ to $C_6$ alkyl group, hydroxy group, cyano group, nitro group, substituted or unsubstituted $C_1$ to $C_6$ alkoxy group, substituted or unsubstituted aryloxy group, $C_1$ to $C_6$ alkylcarbonyl group, $C_1$ to $C_6$ alkoxycarbonyl group, $C_1$ to $C_6$ alkylthio group, amino group, mono- or di-substituted or unsubstituted $C_1$ to $C_6$ alkylamino group, substituted or unsubstituted arylamino group, 4- to 9-membered cyclic amino group that may contain 1 to 3 heteroatoms, formylamino group, $C_1$ to $C_6$ alkylcarbonylamino group, $C_1$ to $C_6$ alkoxycarbonylamino group, $C_1$ to $C_6$ alkylsulfonylamino group, and substituted or unsubstituted arylsulfonylamino group.

The term "substituted or unsubstituted aromatic hydrocarbon group" refers to an aromatic hydrocarbon group (such as benzene ring, naphthalene ring, and anthracene ring) that may have 1 to 5 substituents selected from halogen atom, hydroxy group, cyano group, nitro group, $C_1$ to $C_6$ alkoxy group, $C_1$ to $C_6$ alkylthio group, amino group, mono- or di-substituted $C_1$ to $C_6$ alkylamino group, 4- to 9-membered cyclic amino group that may contain 1 to 3 heteroatoms, formylamino group, $C_1$ to $C_6$ alkylcarbonylamino group, $C_1$ to $C_6$ alkylsulfonylamino group, and substituted or unsubstituted arylsulfonylamino group.

The term "substituted or unsubstituted aromatic heterocyclic ring" refers to an aromatic heterocyclic ring (including a 5- or 6-membered aromatic monocyclic heterocyclic ring or a 9- or 10-membered aromatic condensed heterocyclic ring, such as pyridine ring, pyrimidine ring, pyridazine ring, triazine ring, quinoline ring, naphthylidine ring, quinazoline ring, acridine ring, pyrrole ring, furan ring, thiophene ring, imidazole ring, pyrazole ring, oxazole ring, isoxazole ring, thiazole ring, indole ring, benzofuran ring, benzothiazole ring, benzimidazole ring, and benzoxazole ring, containing 1 to 3 heteroatoms arbitrarily selected from nitrogen, oxygen and sulfur) that may have 1 to 5 substituents selected from halogen atom, hydroxy group, cyano group, nitro group, $C_1$ to $C_6$ alkoxy group, $C_1$ to $C_6$ alkylthio group, amino group, mono- or di-substituted $C_1$ to $C_6$ alkylamino group, 4- to 9-membered cyclic amino group that may contain 1 to 3 heteroatoms, formylamino group, $C_1$ to $C_6$ alkylcarbonylamino group, $C_1$ to $C_6$ alkylsulfonylamino group, and substituted or unsubstituted arylsulfonylamino group.

The term "substituted or unsubstituted aliphatic heterocyclic ring" refers to an aliphatic heterocyclic ring (including 4- to 7-membered aliphatic monocyclic heterocyclic ring or a 9- or 10-membered aliphatic condensed heterocyclic ring, such as azetidine ring, pyrrolidine ring, tetrahydrofuran ring, piperidine ring, morpholine ring, and piperazine ring, containing 1 to 3 heteroatoms arbitrarily selected from nitrogen, oxygen, and sulfur) that may have 1 to 5 substituents selected from halogen atom, substituted or unsubstituted $C_1$ to $C_6$ alkyl group, hydroxy group, cyano group, nitro group, substituted or unsubstituted $C_1$ to $C_6$ alkoxy group, $C_1$ to $C_6$ alkylthio group, amino group, mono- or di-substituted or unsubstituted $C_1$ to $C_6$ alkylamino group, 4- to 9-membered cyclic amino group that may contain 1 to 3 heteroatoms, formylamino group, $C_1$ to $C_6$ alkylcarbonylamino group, $C_1$ to $C_6$ alkoxycarbonylamino group, $C_1$ to $C_6$ alkylsulfonylamino group, and substituted or unsubstituted arylsulfonylamino group.

The term "substituted or unsubstituted $C_1$ to $C_6$ alkoxy group" refers to a $C_1$ to $C_6$ alkoxy group (such as methoxy group, ethoxy group, butoxy group, and hexyloxy group) that may have 1 to 5 substituents selected from halogen atom, hydroxy group, cyano group, $C_1$ to $C_6$ alkoxy group, $C_1$ to $C_6$ alkylthio group, amino group, mono- or di-substituted $C_1$ to $C_6$ alkylamino group, 4- to 9-membered cyclic amino group that may contain 1 to 3 heteroatoms, formylamino group, $C_1$ to $C_6$ alkylcarbonylamino group, $C_1$ to $C_6$ alkylsulfonylamino group, and substituted or unsubstituted arylsulfonylamino group. The term "protective group for an amino group" refers to t-butoxycarbonyl group, benzyloxycarbonyl group, allyloxycarbonyl group, methoxycarbonyl group, ethoxycarbonyl group, 2,2,2-trichloroethoxycarbonyl group, trifluoroacetyl group, acetyl group, benzyl group, and 2,4,6-trimethoxybenzyl group. The term "halogen atom" refers to fluorine atom, chlorine atom, bromine atom and iodine atom.

Preferred examples of the compounds of the present invention include (2S,4S)-1-[[N-(4-ethoxycarbonyl bicyclo[2.2.2]oct-1-yl)amino]acetyl]-4-fluoropyrrolidine-2-carbonitrile, (2S)-1-[[N-(4-ethoxycarbonylbicyclo[2.2.2]oct-1-yl)amino]acetyl]pyrrolidine-2-carbonitrile, (2S)-1-[[N-(4-t-butoxycarbonylbicyclo[2.2.2]oct-1-yl)amino]acetyl]pyrrolidine-2-carbonitrile, (2S,4S)-1-[[N-[4-(2-tetrahydropyranyl)oxycarbonyl bicyclo[2.2.2]oct-1-yl]amino]acetyl]-4-fluoropyrrolidine-2-carbonitrile, (2S)-1-[[N-[4-(2-tetrahydropyranyl)oxycarbonyl bicyclo[2.2.2]oct-1-yl]amino]acetyl]pyrrolidine-2-carbonitrile, (
2S,4S)-1-[[N-(4-ethoxycarbonylbicyclo[2.2.1]hept-1-yl)amino]acetyl]-4-fluoropyrrolidine-2-carbonitrile,
(2S)-1-[[N-(4-ethoxycarbonylbicyclo[2.2.1]hept-1-yl)amino]acetyl]pyrrolidine-2-carbonitrile,
(2S,4S)-1-[[N-(4-benzyloxycarbonylbicyclo[2.2.2]oct-1-yl)amino]acetyl]-4-fluoropyrrolidine-2-carbonitrile,
(2S,4S)-1-[[N-(4-cyclopropylmethyloxycarbonyl bicyclo[2.2.2]oct-1-yl)amino]acetyl]-4-fluoropyrrolidine-2-carbonitrile,
(2S,4S)-4-fluoro-1-[[N-(4-(4-trifluoromethyl)benzyloxycarbonyl bicyclo[2.2.2]oct-1-yl)amino]acetyl]pyrrolidine-2-carbonitrile,
(2S,4S)-4-fluoro-1-[[N-(4-isobutyloxycarbonyl bicyclo[2.2.2]oct-1-yl)amino]acetyl]pyrrolidine-2-carbonitrile,
and (2S,4S)-4-fluoro-1-[[N-(4-isopropyloxycarbonylbicyclo[2.2.2]oct-1-yl)amino]acetyl]pyrrolidine-2-carbonitrile.

Advantage of the Invention

Novel compounds that have high DPP-IV inhibitory activity, the compounds of the present invention are useful agents in the prevention and/or treatment of diabetes and associated complications, as well as in the prevention and/or treatment of diseases involving DPP-IV.

BEST MODE FOR CARRYING OUT THE INVENTION

Figure 1:
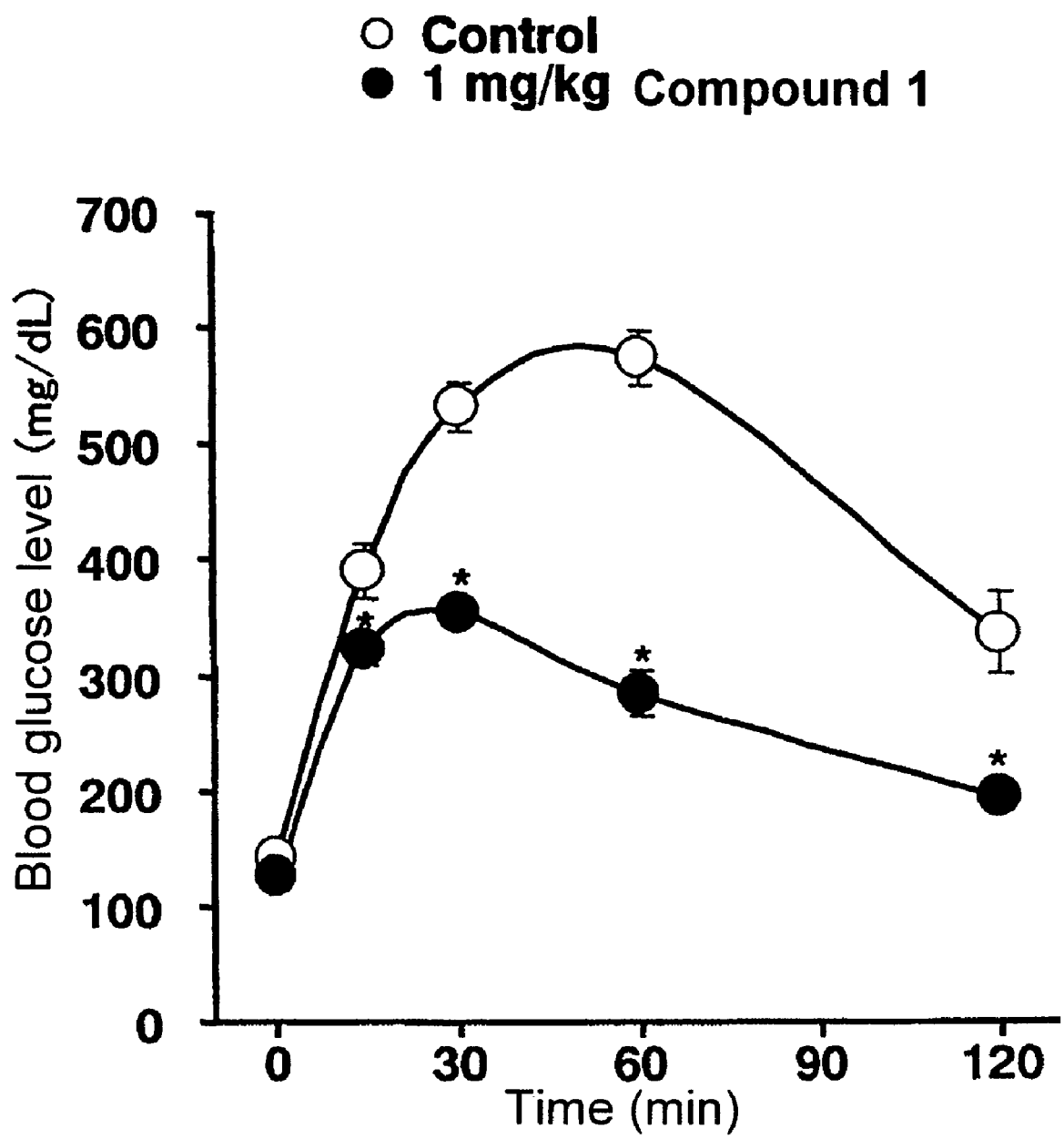
FIG. 1 is a graph showing the results of Test Example 3.

When the compounds of the present invention form pharmaceutically acceptable salts, examples of such a salt include salts with inorganic acids, such as hydrochloric acid, hydrobromic acid, sulfuric acid, nitric acid, and phosphoric acid, or organic acids, such as acetic acid, maleic acid, fumaric acid, succinic acid, lactic acid, malic acid, tartaric acid, citric acid, methanesulfonic acid, p-toluenesulfonic acid, benzenesulfonic acid, salicylic acid, stearic acid, palmitic acid and trifluoroacetic acid; metal salts, such as sodium salt, potassium salt, calcium salt, magnesium salt, aluminum salt, and zinc salt; ammonium salts, such as ammonium salt and tetramethylammonium salt; organic amine salts, such as salts with morpholine and piperidine; and amino acid salts, such as salts with glycine, lysine, arginine, phenylalanine, and proline.

The compounds of the present invention represented by the general formula (1) or salts thereof may contain a single or two or more chiral centers and thus have multiple optical isomers resulting from these chiral centers. Any of these optical isomers and diastereomers are encompassed by the present invention, as are any mixtures thereof in an arbitrary mixing ratio, including racemic mixtures. When the compounds of the present invention represented by the general formula (1) or salts thereof contain a double bond, they may have Z- or E-configuration and any of the mixtures of these compounds in an arbitrary mixing ratio are also encompassed by the present invention. Some of the compounds of the present invention represented by the general formula (1) or salts thereof may have tautomers or rotational isomers, all of which isomers are encompassed by the present invention, as are any of the mixtures thereof in an arbitrary mixing ratio.

The compounds of the present invention represented by the general formula (1) or salts thereof include intramolecular salts, addition products, solvates, and hydrates thereof.

The compounds of the present invention represented by the general formula (1) or salts thereof may be used as a pharmaceutical composition either individually or in conjunction with one or more pharmaceutically acceptable auxiliary agents: They may be formulated with pharmaceutically acceptable carriers or excipients (such as starch, lactose, calcium phosphate, and calcium carbonate), lubricants (such as magnesium stearate, calcium stearate talc, and stearic acid), binders (such as starch, crystalline cellulose, carboxymethylcellulose, gum arabic, polyvinylpyrrolidone, and alginic acid), disintegrating agents (such as talc and carboxymethylcellulose calcium) or diluents (such as saline, aqueous solutions of glucose, mannitol or lactose). Using ordinary techniques, the compounds of the present invention represented by the general formula (1) or salts thereof may be formulated into tablets, capsules, granules, powders, subtle granules, ampoules, or injections for oral or parenteral administration. The compounds of the present invention represented by the general formula (1) or salts thereof are generally administered to humans and other mammals at a dose of 0.0001 to 1000 mg/kg/day while the dose may vary depending on the type of the compound or salt, route of administration, and the age, body weight, and symptoms of the subjects. The compounds of the present invention or salts thereof may be administered in a single daily dose or multiple doses per day.

When necessary, the compounds of the present invention represented by the general formula (1) or salts thereof may be used in conjunction with one or more diabetic therapeutic agents other than DPP-IV inhibitors. Among such diabetic therapeutic agents for use with the compounds of the present invention or salts thereof are insulin and its derivatives, GLP-1 and its derivatives, and other oral diabetic therapeutic agents. Examples of the oral diabetic therapeutic agents include sulfonyl urea diabetic therapeutic agents, non-sulfonylurea insulin secretagogues, biguanide diabetic therapeutic agents, α-glycosidase inhibitors, glucagon antagonists, GLP-1 agonists, PPAR agonists, β3 agonists, SGLT inhibitors, PKC inhibitors, glucagon synthase kinase 3 (GSK-3) inhibitors, protein tyrosine phosphatase 1B (PTP-1B) inhibitors, potassium channel openers, insulin sensitizers, glucose uptake modulators, compounds modifying lipid metabolism, and appetite suppressors.

Examples of GLP-1 and its derivatives include betatropin and NN-2211. Examples of sulfonylurea diabetic therapeutic agents include tolbutamide, glibenclamide, gliclazide, glimepiride, and glipizide. Examples of non-sulfonylurea insulin secretagogues include nateglinide, repaglinide, mitiglinide, and JTT-608. Examples of biguanide diabetic therapeutic agents include metformin. Examples of α-glycosidase inhibitors include voglibose and miglitol. Examples of PPAR agonists include troglitazone, rosiglitazone, pioglitazone, ciglitizone, KRP-297 (MK-767), isaglitazone, GI-262570, and JTT-501. Examples of β3 agonists include AJ-9677, YM-178, and N-5984.

The compounds (1) of the present invention can be produced by various synthetic techniques. The compounds (1) of the present invention can be isolated or purified by common separation means (such as extraction, recrystallization, distillation, and chromatography). The compounds may be obtained in the form of various salts by using common techniques or similar techniques (such as neutralization).

Representative processes for producing the compounds of the present invention and salts thereof will now be described.

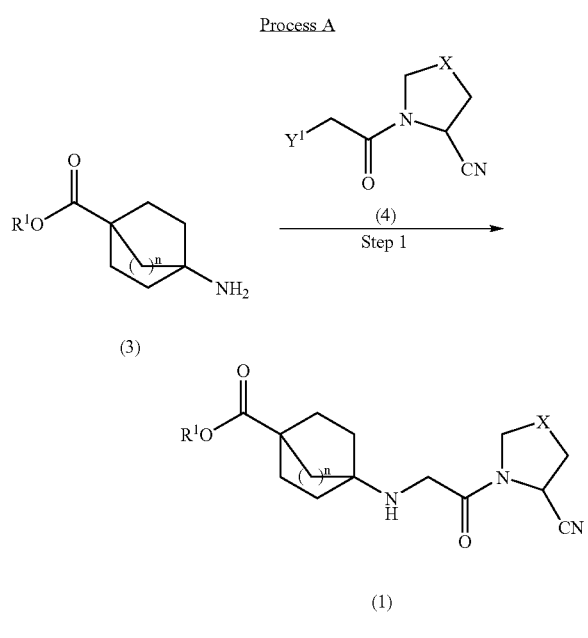

Step 1 (Process A)

In this step, a haloacetic acid derivative of the general formula (4) (where $Y^1$ is Cl or Br, and X is as defined above.) is reacted with a bicycloamine derivative of the general formula (3) (where $R^1$ and n are as defined above.) to obtain a bicycloester derivative of the general formula (1) (where $R^1$, n, and X are as defined above.). The reaction is carried out in the presence or absence of a base. The base for use in this reaction may be an inorganic base, such as sodium hydroxide, potassium hydroxide, sodium bicarbonate, potassium bicarbonate, sodium carbonate, potassium carbonate, and cesium carbonate, or an organic base, such as triethylamine, diisopropylethylamine, N,N,N,N-tetramethylethylenediamine, diazabicyclo[5.4.0]-7-undecene, diazabicyclo[4.3.0]-5-nonene, phosphazene base, and pentaisopropylguanidine. When it is desired to use a catalyst in the reaction, such a catalyst may be a phase transfer catalyst or an inorganic salt, such as tetrabutylammonium bromide, tetrabutylammonium iodide, benzyltriethylammonium bromide, lithium bromide, lithium iodide, sodium iodide, potassium bromide, potassium iodide, cesium bromide, and cesium iodide. The solvent for use in the reaction may be an inert solvent such as acetone, ethanol, toluene, acetonitrile, tetrahydrofuran, dioxane, ethylether, t-butylmethylether, dimethoxyethane, ethyl acetate, dichloromethane, N,N-dimethylformamide, dimethylsulfoxide, and N-methyl-2-pyrrolidone. This reaction proceeds smoothly at 0 to 150° C.

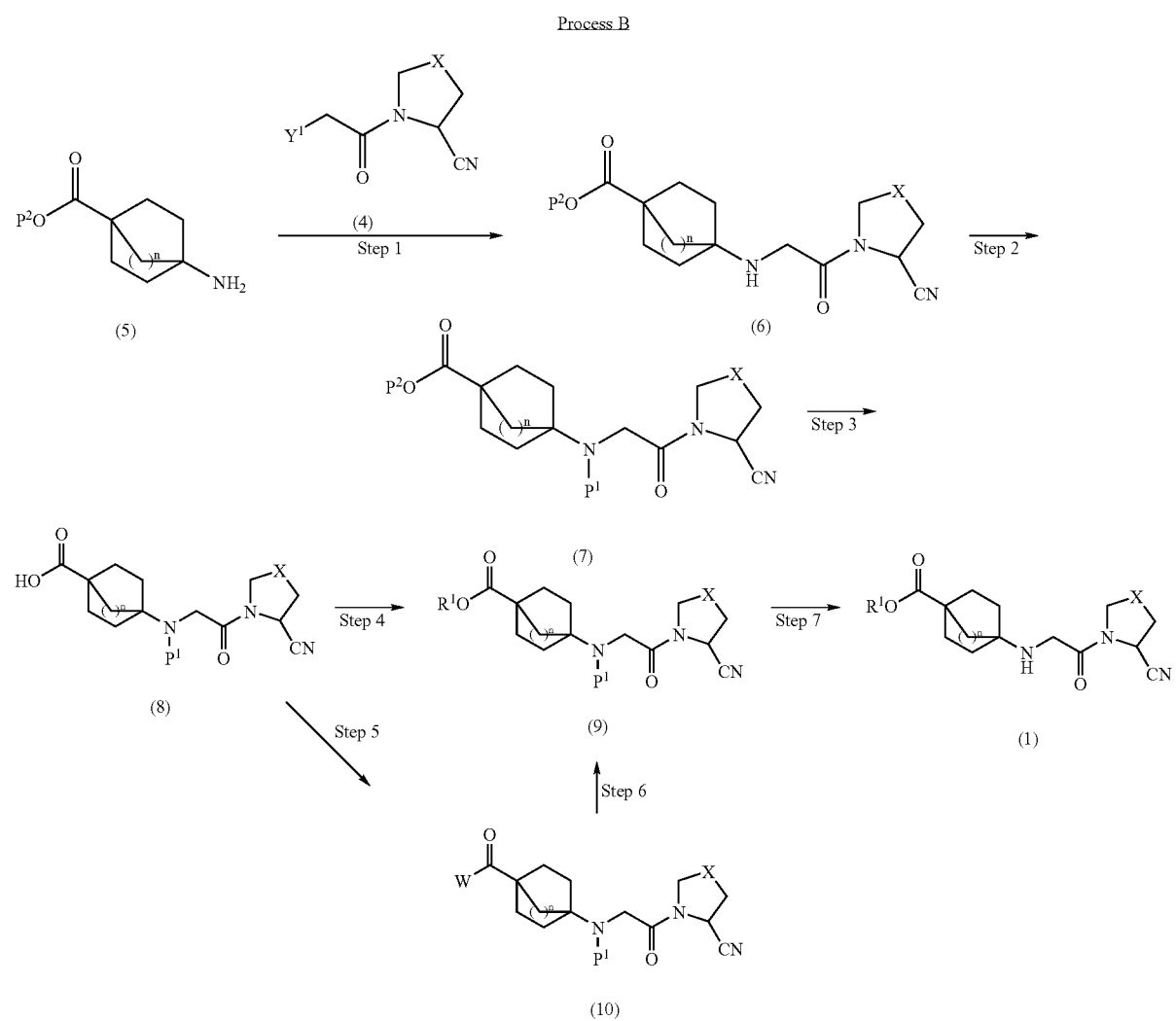

Step 1 (Process B)

In this step, a haloacetic acid derivative of the general formula (4) (where X and $Y^1$ are as defined above.) is reacted with a bicycloamine derivative of the general formula (5) (where $P^2$ is a protective group for a carboxyl group, and n is as defined above.) to obtain a bicycloester derivative of the general formula (6) (where $P^2$, n and X are as defined above.). The reaction is carried out in the presence or absence of a base. The base for use in this reaction may be an inorganic base, such as sodium hydroxide, potassium hydroxide, sodium bicarbonate, potassium bicarbonate, sodium carbonate, potassium carbonate, and cesium carbonate, or an organic base, such as triethylamine, diisopropylethylamine, N,N,N,N-tetramethylethylenediamine, diazabicyclo[5.4.0]-7-undecene, diazabicyclo[4.3.0]-5-nonene, phosphazene base, and pentaisopropylguanidine. When it is desired to use a catalyst in the reaction, the catalyst may be a phase transfer catalyst or an inorganic salt, such as tetrabutylammonium bromide, tetrabutylammonium iodide, benzyltriethylammonium bromide, lithium bromide, lithium iodide, sodium iodide, potassium bromide, potassium iodide, cesium bromide and cesium iodide. The solvent for use in the reaction may be an inert solvent such as acetone, ethanol, toluene, acetonitrile, tetrahydrofuran, dioxane, ethylether, t-butylmethylether, dimethoxyethane, ethyl acetate, dichloromethane, N,N-dimethylformamide, dimethylsulfoxide, and N-methyl-2-pyrrolidone. This reaction proceeds smoothly at 0 to 150° C.

Step 2 (Process B)

In this step, the secondary amino group of the bicycloester derivative of the general formula (6) (where $P^2$, n, and X are as defined above.) is protected to give a bicycloester derivative of the general formula (7) according to claim 2 (where $P^1$ is a protective group for an amino group, and $P^2$, n, and X are as described above.). The protective group $P^1$ for the secondary amine group may be t-butoxycarbonyl group, benzyloxycarbonyl group, or trifluoroacetyl group. The protective groups can be introduced by known techniques: When $P^1$ is t-butoxycarbonyl group, it can be readily introduced by reacting di-t-butyldicarbonate with the bicycloester derivative of the general formula (6) (where $P^2$, n, and X are as defined above.) in the presence or absence of triethylamine or 4-dimethylaminopyridine. When $P^1$ is benzyloxycarbonyl group, it can be readily introduced by reacting benzyloxycarbonyl chloride with the bicycloester derivative of the general formula (6) (where $P^2$, n and X are as defined above.) in the presence of triethylamine, diisopropylethylamine, or potassium carbonate. When $P^1$ is trifluoroacetyl group, it can be readily introduced by reacting trifluoroacetic acid anhydride with the bicycloester derivative of the general formula (6) (where $P^2$, n and X are as defined above.) in the presence of triethylamine or N,N-dimethylaminopyridine.

Step 3 (Process B)

In this step, the $P^2$ group that protects the carboxyl group of the bicycloester derivative of the general formula (7) (where $P^2$, $P^1$, n, and X are as defined above.) is removed to give a bicyclic derivative of the general formula (8) (where $P^1$, n, and X are as defined above.). $P^2$ can be removed by known techniques: When $P^2$ is t-butyl group, it can be readily removed by using trifluoroacetic acid or a solution of hydrogen chloride/dioxane. When $P^2$ is benzyl group, it can be readily removed by using palladium carbon in combination with hydrogen or ammonium formate. When $P^2$ is tetrahydropyranyl group, it can be readily removed by using acetic acid, p-toluenesulfonic acid, or hydrochloric acid.

Step 4 (Process B)

In this step, the bicyclic derivative of the general formula (8) (where $P^1$, n, and X are as defined above.) is esterified or alkylated to obtain a bicycloester derivative of the general formula (9) (where $R^1$, $P^1$, n, and X are as defined above). When the bicycloester derivative of the general formula (9) (where $R^1$, $P^1$, n, and X are as defined above.) is produced by esterification, the bicyclic derivative of the general formula (8) (where $P^1$, n and X are as defined above.) is esterified with an alcohol derivative represented by $R^1OH$ (where $R^1$ is as defined above.) in the presence of a condensation agent to give the bicycloester derivative of the general formula (9) (where $R^1$, $P^1$, n, and X are as defined above.). Examples of the condensation agent for the esterification in this step include dicyclohexylcarbodiimide (DCC), 3-ethyl-1-(3-dimethylaminopropyl)carbodiimide hydrochloride (EDCl), dimethylimidazolinium chloride (DMC), ethyl chloroformate, isobutyl chloroformate, and pivaloyl chloride. These agents may be added in the form of solid, liquid or a solution in a proper solvent. When it is desired to use a base in the condensation reaction, the base may be an alkali carbonate, such as sodium bicarbonate and potassium carbonate, or a tertiary amine, such as triethylamine, diisopropylethylamine, N-methylmorpholine, diazabicyclo[5.4.0]-7-undecene, pyridine, 4-dimethylaminopyridine and 1,8-bis(dimethylamino)naphthalene. The solvent for use in the condensation reaction may be an inert solvent such as N,N-dimethylformamide, N,N-dimethylacetamide, dimethylsulfoxide, acetonitrile, tetrahydrofuran, dioxane, ethyl ether, dimethoxyethane, ethyl acetate, toluene, and dichloromethane. This condensation reaction proceeds smoothly at −20 to 150° C.

When the bicycloester derivative of the general formula (9) (where $R^1$, $P^1$, n, and X are as defined above.) is produced by alkylation, the bicyclic derivative of the general formula (8) (where $P^1$, n, and X are as defined above.) is reacted with a compound represented by $R^1Y^2$ (where $Y^2$ is Cl, Br, I, OMs, OTs or OTf, and $R^1$ is as defined above.) in the presence or absence of a base to give the bicycloester derivative of the general formula (9) (where $R^1$, $P^1$, n, and X are as defined above.) When it is desired to use a base in the reaction, the base may be an alkali carbonate, such as sodium bicarbonate, potassium carbonate, and cesium carbonate, or a tertiary amine, such as triethylamine, diisopropylethylamine, N-methylmorpholine, diazabicyclo[5.4.0]-7-undecene, pyridine, 4-dimethylaminopyridine, and 1,8-bis(dimethylamino)naphthalene, and phosphazene base and pentaisopropylguanidine. When it is desired to use a catalyst in the reaction, the catalyst may be a phase transfer catalyst or inorganic salt, such as tetrabutylammonium bromide, tetrabutylammonium iodide, benzyltriethylammonium bromide, lithium bromide, lithium iodide, sodium iodide, potassium bromide, potassium iodide, cesium bromide, and cesium iodide. The solvent for use in the reaction may be an inert solvent such as acetone, ethanol, N,N-dimethylformamide, N,N-dimethylacetamide, dimethylsulfoxide, acetonitrile, tetrahydrofuran, dioxane, ethylether, dimethoxyethane, ethyl acetate, toluene, and dichloromethane. This reaction proceeds smoothly at −30 to 150° C.

Step 5 (Process B)

In this step, the bicyclic derivative of the general formula (8) (where $P^1$, n, and X are as defined above.) is converted to a bicycloester derivative of the general formula (10) [where W is a reaction residue (such as halogen atoms, and halides, imidazolides, and active esters of carboxylic acids, such as 1-imidazolyl group, 4-nitrophenoxy group, pentafluorophenoxy group, imidoyloxy succinate group and 1-benzotriazolyloxy group (or 1-benzotriazolyl 3-oxide group), $P^1$, n, and X are as described above.]. This step can be readily carried out by known techniques: When W is imidoyloxy succinate group, the bicyclic derivative of the general formula (8) (where $P^1$, n, and X are as defined above.) is reacted with N-hydroxysuccinic acid in the presence of a condensation agent to give the desired product. When W is benzotriazolyloxy group (or 1-benzotriazolyl 3-oxide group), the bicyclic derivative of the general formula (8) (where $P^1$, n, and X are as defined above.) is reacted with 1-hydroxybenzotriazole in the presence of a condensation agent to give the desired product. Examples of the condensation agent for use in this step include dicyclohexylcarbodiimide (DCC), 3-ethyl-1-(3-dimethylaminopropyl)carbodiimide hydrochloride (EDCl), dimethylimidazolinium chloride (DMC), ethyl chloroformate, isobutyl chloroformate, and pivaloyl chloride. These agents may be added in the form of solid, liquid or a solution in a proper solvent. When it is desired to use a base in the condensation reaction, the base may be an alkali carbonate, such as sodium bicarbonate and potassium carbonate, or a tertiary amine, such as triethylamine, diisopropylethylamine, N-methylmorpholine, diazabicyclo[5.4.0]-7-undecene, pyridine, 4-dimethylaminopyridine, and 1,8-bis(dimethylamino) naphthalene. The solvent for use in the condensation reaction may be an inert solvent such as N,N-dimethylformamide, N,N-dimethylacetamide, dimethylsulfoxide, acetonitrile, tetrahydrofuran, dioxane, ethyl ether, dimethoxyethane, ethyl acetate, toluene, and dichloromethane. This condensation reaction proceeds smoothly at −20 to 150° C. The resulting bicyclic derivative of the general formula (10) (where W, $P^1$, n, and X are as described above.) may be used in the subsequent step after carrying out isolation and purification or as the unpurified crude product.

Step 6 (Process B)

In this step, the bicyclic derivative of the general formula (10) (where W, $P^1$, n, and X are as described above.) is reacted with an alcohol derivative represented by $R^1OH$ (where $R^1$ is as defined above.) to give a bicycloester derivative of the general formula (9) (where $R^1$, $P^1$, n, and X are as defined above.). When a base is used in the reaction, the base may be an inorganic salt, such as sodium hydroxide, potassium hydroxide, sodium bicarbonate, potassium bicarbonate, sodium carbonate, potassium carbonate, and cesium carbonate, or an organic base, such as triethylamine, diisopropylethylamine, N,N,N,N-tetramethylethylenediamine, diazabicyclo[5.4.0]-7-undecene, diazabicyclo[4.3.0]-5-nonene, 4-dimethylaminopyridine, phosphazene base, and pentaisopropylguanidine. The solvent for use in the reaction may be an inert solvent such as toluene, acetonitrile, tetrahydrofuran, dioxane, ethylether, t-butylmethylether, dimethoxyethane, ethyl acetate, dichloromethane, N,N-dimethylformamide, dimethylsulfoxide, and N-methyl-2-pyrrolidone. This reaction proceeds smoothly at −30 to 150° C.

Step 7 (Process B)

In this step, the $P^1$ group that protects the secondary amino group in the bicycloester derivative of the general formula (9) (where $R^1$, $P^1$, n, and X are as defined above.) is removed to give a bicycloester derivative of the general formula (1) (where $R^1$, n, and X are as defined above). $P^1$ can be removed by known techniques: When $P^1$ is t-butoxycarbonyl group, it can be readily removed by using trifluoroacetic acid or a solution of hydrogen chloride/dioxane. When $P^1$ is benzyloxycarbonyl group, it can be readily removed by using palladium carbon in combination with hydrogen or ammonium formate. When $P^1$ is trifluoroacetyl group, it can be readily removed by using an ammonia/methanol solution.

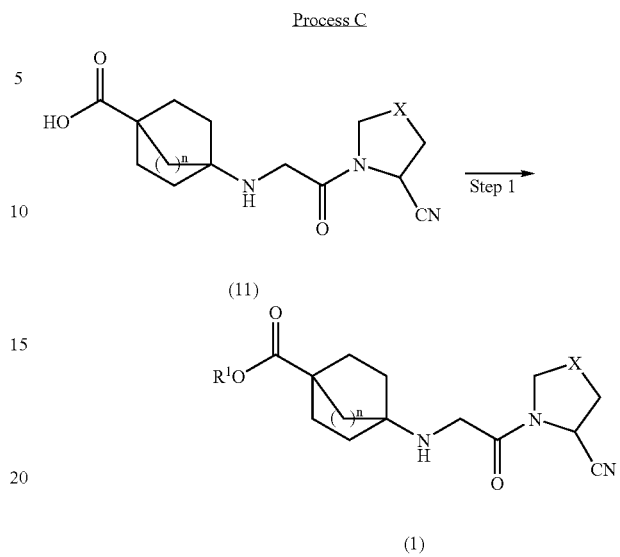

Step 1 (Process C)

In this step, a bicycloester derivative of the general formula (1) (where $R^1$, n, and X are as defined above.) is obtained through esterification or alkylation. When the bicycloester derivative of the general formula (1) (where $R^1$, n, and X are as defined above.) is obtained through esterification, a bicyclic derivative of the general formula (11) (where n and X are as defined above.) is esterified with an alcohol derivative represented by $R^1OH$ (where $R^1$ is as defined above.) in the presence of a condensation agent to give the bicycloester derivative of the general formula (1) (where $R^1$, n, and X are as defined above.). Examples of the condensation agent for use in the esterification include dicyclohexylcarbodiimide (DCC), 3-ethyl-1-(3-dimethylaminopropyl)carbodiimide hydrochloride (EDCl), dimethylimidazolinium chloride (DMC), ethyl chloroformate, isobutyl chloroformate, and pivaloyl chloride. These agents may be added in the form of solid, liquid or a solution in a proper solvent. When it is desired to use a base in the condensation reaction, the base may be an alkali carbonate, such as sodium bicarbonate and potassium carbonate, or a tertiary amine, such as triethylamine, diisopropylethylamine, N-methylmorpholine, diazabicyclo[5.4.0]-7-undecene, pyridine, 4-dimethylaminopyridine, and 1,8-bis(dimethylamino)naphthalene. The solvent for use in the condensation reaction may be an inert solvent such as N,N-dimethylformamide, N,N-dimethylacetamide, dimethylsulfoxide, acetonitrile, tetrahydrofuran, dioxane, ethyl ether, dimethoxyethane, ethyl acetate, toluene, and dichloromethane. This condensation reaction proceeds smoothly at −20 to 150° C. Alternatively, the condensation reaction may be carried out via an active ester or acid chloride having 1-imidazolyl group, 4-nitrophenoxy group, pentafluorophenoxy group, imidoyloxy succinate group or 1-benzotriazolyloxy group (or 1-benzotriazolyl 3-oxide group). In such a case, the active ester or acid chloride may be used in the subsequent step after carrying out isolation and purification or as the unpurified crude product.

When the bicycloester derivative of the general formula (1) (where $R^1$, n, and X are as defined above.) is obtained through alkylation, a bicyclic derivative of the general formula (11) (where n and X are as defined above.) is reacted with a compound represented by $R^1Y^2$ (where $Y^2$ and $R^1$ are as described above.) in the presence or absence of a base to give the bicycloester derivative of the general formula (1) (where $R^1$, n, and X are as defined above.). When it is desired to use a base in the reaction, the base may be an alkali carbonate, such as sodium bicarbonate, potassium carbonate, and cesium carbonate, or a tertiary amine, such as triethylamine, diisopropylethylamine, N-methylmorpholine, diazabicyclo[5.4.0]-7-undecene, pyridine, 4-dimethylaminopyridine, and 1,8-bis(dimethylamino)naphthalene, and phosphazene base and pentaisopropylguanidine. When it is desired to use a catalyst in the reaction, the catalyst may be a phase transfer catalyst or inorganic salt, such as tetrabutylammonium bromide, tetrabutylammonium iodide, benzyltriethylammonium bromide, lithium bromide, lithium iodide, sodium iodide, potassium bromide, potassium iodide, cesium bromide and cesium iodide. The solvent for use in the reaction may be an inert solvent such as acetone, ethanol, N,N-dimethylformamide, N,N-dimethylacetamide, dimethylsulfoxide, acetonitrile, tetrahydrofuran, dioxane, ethylether, dimethoxyethane, ethyl acetate, toluene, and dichloromethane. This reaction proceeds smoothly at −30 to 150° C.

The advantageous features of the present invention will now be described with reference to experiments and examples, which are not intended to limit the scope of the invention in any way.

REFERENCE EXAMPLE 1

Synthesis of ethyl 4-aminobicyclo[2.2.2]octane-1-carboxylate

Step 1:

Synthesis of methyl 4-benzyloxycarbonylaminobicyclo[2.2.2]octane-1-carboxylate

Methyl hydrogen bicyclo[2.2.2]octane-1,4-dicarboxylate (25.0 g), diphenylphosphoryl azide (32.5 g), triethylamine (17.3 mL) and toluene (50.0 mL) were mixed together. The mixture was stirred for 2 hours at room temperature and was heated and refluxed for 2 hours. To the resulting mixture, benzylalcohol (122 mL) was added and the mixture was further heated and refluxed for 17 hours. Subsequently, the mixture was allowed to cool and was sequentially washed with a 10% aqueous citric acid, saturated aqueous solution of sodium bicarbonate, and saturated brine. The mixture was then dried over anhydrous sodium sulfate and concentrated under reduced pressure. The residue was purified by silica gel column chromatography (eluant: hexane:ethyl acetate=2:1) to give methyl 4-benzyloxycarbonylaminobicyclo[2.2.2]octane-1-carboxylate (32.2 g).

MS (FAB$^+$) m/z: 318 (MH$^+$).

Step 2:

Synthesis of 4-benzyloxycarbonylaminobicyclo[2.2.2]octane-1-carboxylic acid

Methyl 4-benzyloxycarbonylaminobicyclo[2.2.2]octane-1-carboxylate (64.3 g) was dissolved in ethanol (1100 mL). To this solution, a 1 mol/L aqueous solution of sodium hydroxide (1000 mL) was added and the mixture was stirred at 50° C. for 1 hour. Ethanol in the mixture was evaporated under reduced pressure and the residue was washed with diethylether (500 mL), followed by addition of concentrated hydrochloric acid to adjust the pH to acidic (pH 1). The resulting crystals were filtrated, washed with water, and dried under reduced pressure to give 4-benzyloxycarbonylaminobicyclo[2.2.2]octane-1-carboxylic acid (56.1 g).

MS (FAB$^+$) m/z: 304 (MH$^+$).

Step 3:

Synthesis of ethyl 4-benzyloxycarbonylaminobicyclo[2.2.2]octane-1-carboxylate

4-Benzyloxycarbonylaminobicyclo[2.2.2]octane-1-carboxylic acid (56.0 g) was dissolved in N,N-dimethylformamide (1000 mL). To this solution, sodium bicarbonate (46.6 g) and then ethyl iodide (22.2 mL) were added and the mixture was stirred at 50 to 60° C. for 5 hours. Subsequently, additional sodium bicarbonate (46.6 g) and ethyl iodide (22.2 mL) were added and the mixture was stirred for additional 3 hours. The insoluble materials in the mixture were filtered and the filtrate was concentrated under reduced pressure. The residue was dissolved in ethyl acetate (700 mL) and the solution was washed with water, dried over anhydrous sodium sulfate, and dried under reduced pressure. The resulting residue was purified by silica gel column chromatography (eluant: hexane:ethyl acetate=2:1→ethyl acetate) to give ethyl 4-benzyloxycarbonylaminobicyclo[2.2.2]octane-1-carboxylate (56.8 g).

MS (FAB$^+$) m/z: 332 (MH$^+$).

Step 4:

Synthesis of ethyl 4-aminobicyclo[2.2.2]octane-1-carboxylate

Ethyl 4-benzyloxycarbonylaminobicyclo[2.2.2]octane-1-carboxylate (40.0 g) was dissolved in ethanol (400 mL). To this solution, 10% palladium-carbon (4.00 g) was added and the mixture was stirred at room temperature for 6 hours in a stream of hydrogen. The catalyst in the reaction mixture was filtered through a Celite pad and the filtered catalyst, together with the Celite pad, was washed with ethanol. The filtrate and the washings were combined and concentrated under reduced pressure. The resulting residue was dried under reduced pressure to give ethyl 4-aminobicyclo[2.2.2]octane-1-carboxylate (23.9 g).

MS (EI$^+$) m/z: 197 (M$^+$).

REFERENCE EXAMPLE 2

Synthesis of 1,1-dimethylethyl 4-aminobicyclo[2.2.2]octane-1-carboxylate

Step 1:

Synthesis of 1,1-dimethylethyl methyl bicyclo[2.2.2]octane-1,4-dicarboxylate

Methyl hydrogen bicyclo[2.2.2]octane-1,4-dicarboxylate (500 mg) was dissolved in dichloromethane (5 mL) and sulfuric acid (50 μL) was added to the solution. The mixture was bubbled with isobutene for 5 minutes while chilled in a salt/ice bath. The mixture was then stirred for 4 hours at room temperature and was left for 4 days. Subsequently, the reaction mixture was diluted with dichloromethane (5 mL), washed sequentially with a saturated aqueous solution of sodium bicarbonate and saturated brine, dried over anhydrous sodium sulfate, and concentrated under reduced pressure.

The residue was dried under reduced pressure to give 1,1-dimethylethyl methyl bicyclo[2.2.2]octane-1,4-dicarboxylate (497 mg).

MS (FAB$^+$) m/z: 269 (MH$^+$)

Step 2:

Synthesis of 1,1-dimethylethyl hydrogen bicyclo[2.2.2]octane-1,4-dicarboxylate 1,1-Dimethylethyl methyl bicyclo[2.2.2]octane-1,4-dicarboxylate (495 mg) was dissolved in methanol (5 mL). To this solution, a 2 mol/L aqueous sodium hydroxide solution (0.92 mL) was added and the mixture was stirred at room temperature for 8 hours and then at 50° C. for 2 hours. Methanol in the mixture was evaporated under reduced pressure. Water was added to the resulting residue and the mixture was washed with diethyl ether and was neutralized with 3 mol/L hydrochloric acid. The resulting crystals were filtered, washed with water, and dried under reduced pressure to give 1,1-dimethylethyl hydrogen bicyclo[2.2.2]octane-1,4-dicarboxylate (344 mg).

$^1$H NMR (CDCl$_3$) δ 1.41 (s, 9H), 1.72-1.87 (m, 12H)

Step 3:

Synthesis of 1,1-dimethylethyl 4-benzyloxycarbonylaminobicyclo[2.2.2]octane-1-carboxylate Using 1,1-dimethylethyl hydrogen bicyclo[2.2.2]octane-1,4-dicarboxylate (340 mg), the same procedure was followed as in Step 1 of Reference Example 1 to give 1,1-dimethylethyl 4-benzyloxycarbonylaminobicyclo[2.2.2]octane-1-carboxylate (433 mg).

$^1$H NMR (CDCl$_3$) δ 1.41 (s, 9H), 1.84 (s, 12H), 4.48-4.62 (br, 1H), 5.03 (s, 2H), 7.28-7.38 (m, 5H).

Step 4:

Synthesis of 1,1-dimethylethyl 4-aminobicyclo[2.2.2]octane-1-carboxylate

Using 1,1-dimethylethyl 4-benzyloxycarbonylamino bicyclo[2.2.2]octane-1-carboxylate (425 mg), the same procedure was followed as in Step 4 of Reference Example 1 to give 1,1-dimethylethyl 4-aminobicyclo[2.2.2]octane-1-carboxylate (218 mg).

$^1$H NMR (CDCl$_3$) δ 1.41 (s, 9H), 1.52-1.56 (m, 6H), 1.80-1.84 (m, 6H).

REFERENCE EXAMPLE 3

Synthesis of 2-tetrahydropyranyl 4-aminobicyclo[2.2.2]octane-1-carboxylate

Step 1:

Synthesis of 2-tetrahydropyranyl 4-benzyloxycarbonylamino bicyclo[2.2.2]octane-1-carboxylate 4-Benzyloxycarbonylaminobicyclo[2.2.2]octane-1-carboxylic acid (1.00 g) was suspended in dichloromethane (10 mL). To this suspension, 3,4-dihydro-2H-pyran (1.20 mL) and then p-toluenesulfonic acid monohydrate (6.3 mg) were added and the mixture was stirred at room temperature for 30 minutes. Subsequently, the reaction mixture was sequentially washed with a saturated aqueous sodium bicarbonate solution and water, dried over anhydrous sodium sulfate, and concentrated under reduced pressure. The residue was purified by silica gel column chromatography (eluant: hexane:ethyl acetate=4:1) to give 2-tetrahydropyranyl 4-benzyloxycarbonylaminobicyclo[2.2.2]octane-1-carboxylate (1.18 g).

$^1$H NMR (CDCl$_3$) δ 1.53-1.95 (m, 18H), 3.67-3.71 (m, 1H), 3.82-3.89 (m, 1H), 4.59 (br, 1H), 5.03 (s, 2H), 5.95 (br, 1H), 7.29-7.38 (m, 5H).

Step 2:

Synthesis of 2-tetrahydropyranyl 4-aminobicyclo[2.2.2]octane-1-carboxylate

Using 2-tetrahydropyranyl 4-benzyloxycarbonylaminobicyclo[2.2.2]octane-1-carboxylate (548 mg), the same procedure was followed as in Step 4 of Reference Example 1 to give 2-tetrahydropyranyl 4-aminobicyclo[2.2.2]octane-1-carboxylate (357 mg).

MS (EI$^+$) m/z: 253 (M$^+$).

REFERENCE EXAMPLE 4

Synthesis of (2S,4S)-1-(2-chloroacetyl)-4-fluoropyrrolidine-2-carbonitrile

According to the production process of (2S,4S)-1-(2-bromoacetyl)-4-fluoropyrrolidine-2-carbonitrile described in WO 02/38541 pamphlet, (2S,4S)-4-fluoropyrrolidine-2-carboxamide hydrochloride (5.00 g) and chloroacetyl chloride (2.60 mL) were used to obtain (2S,4S)-1-(2-chloroacetyl)-4-fluoropyrrolidine-2-carbonitrile (4.96 g).

MS (EI$^+$) m/z: 190 (M$^+$).

HRMS (EI$^+$) for C$_7$H$_8$ClFN$_2$O(M$^+$): calcd, 190.0309; found, 190.0283.

EXAMPLE 1

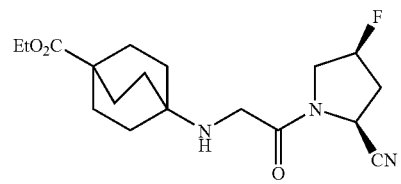

Synthesis of (2S,4S)-1-[[N-(4-ethoxycarbonyl bicyclo[2.2.2]oct-1-yl)amino]acetyl]-4-fluoropyrrolidine-2-carbonitrile Ethyl 4-aminobicyclo[2.2.2]octane-1-carboxylate (92.0 mg) was dissolved in acetonitrile (2 mL) and diisopropylamine (100 μL) was added to the solution. While the mixture was chilled in an ice bath, (2S,4S)-1-(2-bromoacetyl)-4-fluoropyrrolidine-2-carbonitrile (100 mg) in acetonitrile (1 mL) was added dropwise. The mixture was stirred for 1.5 hours while chilled in the ice bath. Subsequently, water was added and the mixture was extracted with ethyl acetate. The ethyl acetate layer was washed with saturated brine, dried over anhydrous sodium sulfate, and concentrated under reduced pressure. The residue was purified by silica gel column chromatography (eluant: ethyl acetate:methanol=5:1) to give (2S,4S)-1-[[N-(4-ethoxycarbonylbicyclo[2.2.2]oct-1-yl)amino]acetyl]-4-fluoropyrrolidine-2-carbonitrile (132 mg).

MS (EI+) m/z: 351 (M+)

HRMS (EI+) for $C_{18}H_{26}FN_3O_3$ (M+): calcd, 351.1958; found, 351.1982.

EXAMPLE 2

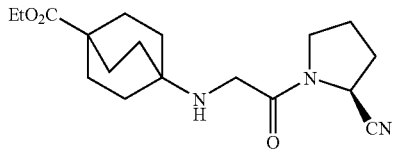

Synthesis of (2S)-1-[[N-(4-ethoxycarbonylbicyclo[2.2.2]oct-1-yl)amino]acetyl]pyrrolidine-2-carbonitrile Ethyl 4-aminobicyclo[2.2.2]octane-1-carboxylate (115 mg) was dissolved in N,N-dimethylformamide (1.5 mL) and diisopropylethylamine (100 μL) was added to the solution. (2S)-1-(2-Bromoacetyl)pyrrolidine-2-carbonitrile (120 mg) in N,N-dimethylformamide (1 mL) was then added dropwise at room temperature. The mixture was stirred for 2 hours at room temperature and was concentrated under reduced pressure. The residue was purified by silica gel column chromatography (eluant: chloroform: methanol=10:1) to give (2S)-1-[[N-(4-ethoxycarbonylbicyclo[2.2.2]oct-1-yl)amino]acetyl]pyrrolidine-2-carbonitrile (95.1 mg).

MS (EI+) m/z: 333 (M+).

HRMS (EI+) for $C_{18}H_{27}N_3O_3$ (M+): calcd, 333.2052; found, 333.2037.

EXAMPLE 3

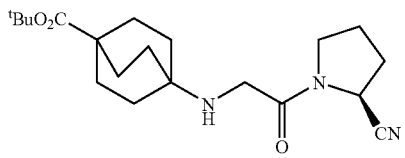

Synthesis of (2S)-1-[[N-(4-t-butoxycarbonylbicyclo[2.2.2]oct-1-yl)amino]acetyl]pyrrolidine-2-carbonitrile In a similar manner to Example 2, t-butyl 4-aminobicyclo[2.2.2]octane-1-carboxylate (100 mg) and (2S)-1-(2-bromoacetyl)pyrrolidine-2-carbonitrile (90.0 mg) were used to obtain (2S)-1-[[N-(4-t-butoxycarbonylbicyclo[2.2.2]oct-1-yl)amino]acetyl]pyrrolidine-2-carbonitrile (97.6 mg).

MS (EI+) m/z: 361 (M+).

HRMS (EI+) for $C_{20}H_{31}N_3O_3$ (M+): calcd, 361.2365; found, 361.2373.

EXAMPLE 4

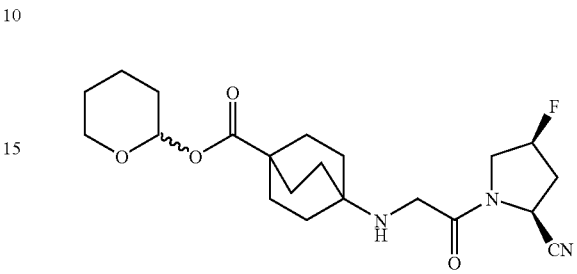

Synthesis of (2S,4S)-1-[[N-[4-(2-tetrahydropyranyl)oxycarbonyl bicyclo[2.2.2]oct-1-yl]amino]acetyl]-4-fluoropyrrolidine-2-carbonitrile In a similar manner to Example 2,2-tetrahydropyranyl 4-aminobicyclo[2.2.2]octane-1-carboxylate (62.9 mg) and (2S,4S)-1-(2-bromoacetyl)-4-fluoropyrrolidine-2-carbonitrile (53.1 mg) were used to obtain (2S,4S)-1-[[N-[4-(2-tetrahydropyranyl)oxycarbonylbicyclo[2.2.2]oct-1-yl]amino]acetyl]-4-fluoropyrrolidine-2-carbonitrile (73.3 mg).

MS (FAB+) m/z: 408 (MH+).

HRMS (FAB+) for $C_{21}H_{31}FN_3O_4$ (MH+): calcd, 408.2299; found, 408.2295.

EXAMPLE 5

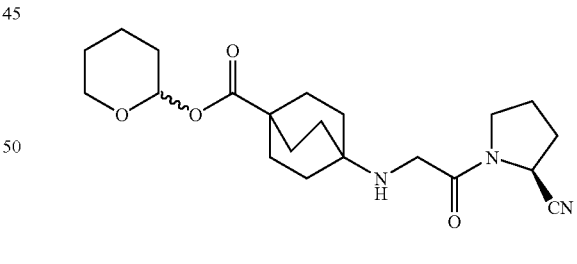

Synthesis of (2S)-1-[[N-[4-(2-tetrahydropyranyl)oxycarbonyl bicyclo[2.2.2]oct-1-yl]amino]acetyl]pyrrolidine-2-carbonitrile In a similar manner to Example 2,2-tetrahydropyranyl 4-aminobicyclo[2.2.2]octane-1-carboxylate (90.0 mg) and (2S)-1-(2-bromoacetyl)pyrrolidine-2-carbonitrile (70.0 mg) were used to obtain (2S)-1-[[N-[4-(2-tetrahydropyranyl)oxycarbonyl bicyclo[2.2.2]oct-1-yl]amino]acetyl]pyrrolidine-2-carbonitrile (85.2 mg).

MS (EI+) m/z: 389 (M+).

HRMS (EI+) for $C_{21}H_{31}N_3O_4$ (M+): calcd, 389.2315; found, 389.2296.

EXAMPLE 6

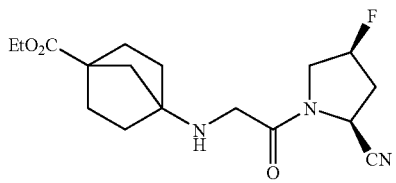

Synthesis of (2S,4S)-1-[[N-(4-ethoxycarbonyl bicyclo[2.2.1]hept-1-yl)amino]acetyl]-4-fluoropyrrolidine-2-carbonitrile Ethyl 4-aminobicyclo[2.2.1]heptane-1-carboxylate (50.0 mg) was dissolved in N,N-dimethylformamide (2 mL) and potassium-carbonate (40.0 mg) was added to the solution. (2S,4S)-1-(2-Bromoacetyl)-4-fluoropyrrolidine-2-carbonitrile (64.2 mg) in N,N-dimethylformamide (1 mL) was then added dropwise at room temperature and the mixture was stirred for 1 hour. The insoluble materials were filtered and the filtrate was concentrated. The resulting residue was purified by silica gel column chromatography (NH silica, eluant: ethyl acetate) to give (2S,4S)-1-[[N-(4-ethoxycarbonylbicyclo[2.2.1]hept-1-yl)amino]acetyl]-4-fluoropyrrolidine-2-carbonitrile (89.0 mg).

MS (FAB+) m/z: 338 (MH+).

HRMS (FAB+) for $C_{17}H_{25}FN_3O_3$ (MH+): calcd, 338.1880; found, 338.1835.

EXAMPLE 7

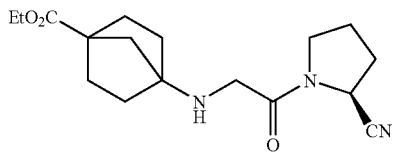

Synthesis of (2S)-1-[[N-(4-ethoxycarbonylbicyclo[2.2.1]hept-1-yl)amino]acetyl]pyrrolidine-2-carbonitrile In a similar manner to Example 6, ethyl 4-aminobicyclo[2.2.1]heptane-1-carboxylate (50.0 mg) and (2S)-1-(2-bromoacetyl)pyrrolidine-2-carbonitrile (59.3 mg) were used to obtain (2S)-1-[[N-(4-ethoxycarbonylbicyclo[2.2.1]hept-1-yl)amino]acetyl]pyrrolidine-2-carbonitrile (79.4 mg).

MS (FAB+) m/z: 320 (MH+).

HRMS (FAB+) for $C_{17}H_{26}N_3O_3$ (MH+): calcd, 320.1974; found, 320.1975.

EXAMPLE 8

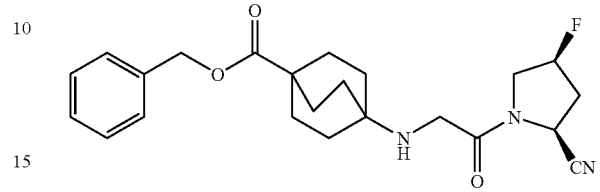

Synthesis of (2S,4S)-1-[[N-(4-benzyloxycarbonyl bicyclo[2.2.2]oct-1-yl)amino]acetyl]-4-fluoropyrrolidine-2-carbonitrile (2S,4S)-1-[[N-(4-Carboxybicyclo[2.2.2]oct-1-yl)amino]acetyl]-4-fluoropyrrolidine-2-carbonitrile (30.0 mg) was dissolved in N,N-dimethylformamide (1.0 mL) and cesium carbonate (45.3 mg) was added to the solution. Benzyl bromide (17.5 mg) in N,N-dimethylformamide (0.5 mL) was then added while the mixture was chilled in an ice bath and the mixture was stirred for 1 hour. Subsequently, water was added and the mixture was extracted with ethyl acetate. The ethyl acetate layer was washed with water and saturated brine, dried over anhydrous sodium sulfate, and concentrated under reduced pressure. The resulting residue was purified by silica gel column chromatography (eluant: dichloromethane:methanol=10:1) to give (2S,4S)-1-[[N-(4-benzyloxycarbonyl bicyclo[2.2.2]oct-1-yl)amino]acetyl]-4-fluoropyrrolidine-2-carbonitrile (30.6 mg).

MS (FAB+) m/z: 414 (MH+).

HRMS (FAB+) for $C_{23}H_{29}FN_3O_3$ (MH+): calcd, 414.2193; found, 414.2176.

EXAMPLE 9

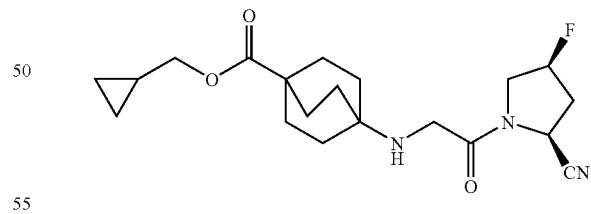

Synthesis of (2S,4S)-1-[[N-(4-cyclopropylmethyloxycarbonyl bicyclo[2.2.2]oct-1-yl)amino]acetyl]-4-fluoropyrrolidine-2-carbonitrile In a similar manner to Example 8, (2S,4S)-1-[[N-(4-carboxybicyclo[2.2.2]oct-1-yl)amino]acetyl]-4-fluoropyrrolidine-2-carbonitrile (20.0 mg) and cyclopropylmethyl bromide (12.8 mg) were used to obtain (2S,4S)-1-[[N-(4-cyclopropylmethyloxycarbonylbicyclo[2.2.2]oct-1-yl)amino]acetyl]-4-fluoropyrrolidine-2-carbonitrile (13.7 mg).

MS (FAB+) m/z: 378 (MH+).

HRMS (FAB+) for $C_{20}H_{29}FN_3O_3$ (MH+): calcd, 378.2193; found, 378.2207.

EXAMPLE 10

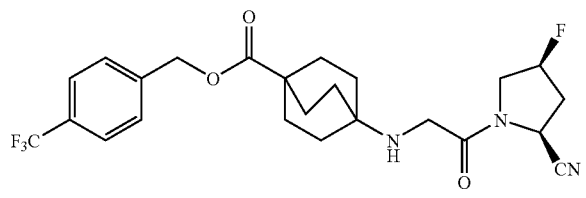

Synthesis of (2S,4S)-4-fluoro-1-[[N-[4-(4-trifluoromethylbenzyl)oxycarbonylbicyclo[2.2.2]oct-1-yl]amino]acetyl]pyrrolidine-2-carbonitrile In a similar manner to Example 8, (2S,4S)-1-[[N-(4-carboxybicyclo[2.2.2]oct-1-yl)amino]acetyl]-4-fluoropyrrolidine-2-carbonitrile (20.0 mg) and 4-trifluoromethylbenzyl bromide (16.2 mg) were used to obtain (2S,4S)-4-fluoro-1-[[N-[4-(4-trifluoromethylbenzyl)oxycarbonyl bicyclo[2.2.2]oct-1-yl]amino]acetyl]pyrrolidine-2-carbonitrile (22.2 mg).

MS (FAB+) m/z: 482 (MH+).

HRMS (FAB+) for $C_{24}H_{28}F_4N_3O_3$ (MH+): calcd, 482.2067; found, 482.2068.

EXAMPLE 11

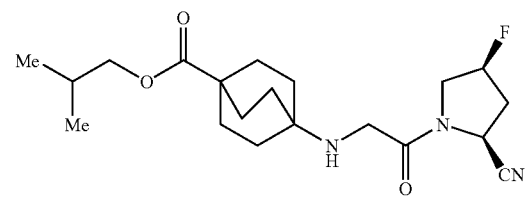

Synthesis of (2S,4S)-4-fluoro-1-[[N-[4-(2-methylpropyl)oxycarbonylbicyclo[2.2.2]oct-1-yl]amino]acetyl]pyrrolidine-2-carbonitrile In a similar manner to Example 8, (2S,4S)-1-[[N-(4-carboxybicyclo[2.2.2]oct-1-yl)amino]acetyl]-4-fluoropyrrolidine-2-carbonitrile (20.0 mg) and isobutyl bromide (9.3 mg) were used to obtain (2S,4S)-4-fluoro-1-[[N-[4-(2-methylpropyl)oxycarbonylbicyclo[2.2.2]oct-1-yl]amino]acetyl]pyrrolidine-2-carbonitrile (14.2 mg).

MS (FAB+) m/z: 380 (MH+).

HRMS (FAB+) for $C_{20}H_{31}FN_3O_3$ (MH+): calcd, 380.2349; found, 380.2361.

EXAMPLE 12

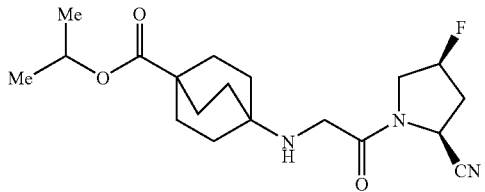

Synthesis of (2S,4S)-4-fluoro-1-[[N-[4-(2-methylethyl)oxycarbonylbicyclo[2.2.2]oct-1-yl]amino]acetyl]pyrrolidine-2-carbonitrile In a similar manner to Example 8, (2S,4S)-1-[[N-(4-carboxybicyclo[2.2.2]oct-1-yl)amino]acetyl]-4-fluoropyrrolidine-2-carbonitrile (20.0 mg) and isopropyl iodide (10.5 mg) were used to obtain (2S,4S)-4-fluoro-1-[[N-[4-(2-methylethyl)oxycarbonylbicyclo[2.2.2]oct-1-yl]amino]acetyl]pyrrolidine-2-carbonitrile (11.2 mg).

MS (EI+) m/z: 365 (M+).

HRMS (EI+) for $C_{19}H_{28}FN_3O_3$ (M+): calcd, 365.2115; found, 365.2096.

EXAMPLE 13

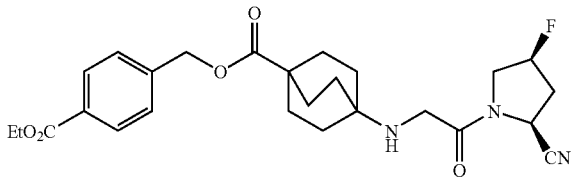

Synthesis of (2S,4S)-1-[[N-[4-(4-ethoxycarbonylbenzyl)oxycarbonylbicyclo[2.2.2]oct-1-yl]amino]acetyl]-4-fluoropyrrolidine-2-carbonitrile In a similar manner to Example 8, (2S,4S)-1-[[N-(4-carboxybicyclo[2.2.2]oct-1-yl)amino]acetyl]-4-fluoropyrrolidine-2-carbonitrile (32.3 mg) and 4-ethoxycarbonylbenzyl bromide (28.1 mg) were used to obtain (2S,4S)-1-[[N-[4-(4-ethoxycarbonylbenzyl)oxycarbonyl bicyclo[2.2.2]oct-1-yl]amino]acetyl]-4-fluoropyrrolidine-2-carbonitrile (34.7 mg).

MS (EI+) m/z: 485 (M+).

HRMS (EI+) for $C_{26}H_{32}FN_3O_5$ (M+): calcd, 485.2326; found, 485.2309.

EXAMPLE 14

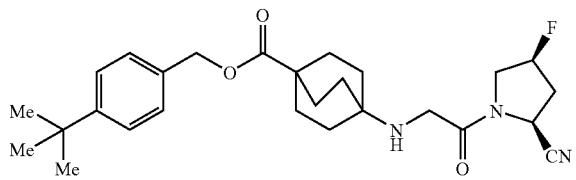

Synthesis of (2S,4S)-1-[[N-[4-[4-(2,2-dimethylethyl)benzyl]oxycarbonylbicyclo[2.2.2]oct-1-yl]amino]acetyl]-4-fluoropyrrolidine-2-carbonitrile In a similar manner to Example 8, (2S,4S)-1-[[N-(4-carboxybicyclo[2.2.2]oct-1-yl)amino]acetyl]-4-fluoropyrrolidine-2-carbonitrile (30.0 mg) and 4-(2,2-dimethylethyl)benzyl bromide (23.2 mg) were used to obtain (2S,4S)-1-[[N-[4-[4-(2,2-dimethylethyl)benzyl]oxycarbonyl bicyclo[2.2.2]oct-1-yl]amino]acetyl]-4-fluoropyrrolidine-2-carbonitrile (29.9 mg).

MS (FAB+) m/z: 470 (MH+).

HRMS (FAB+) for $C_{27}H_{37}FN_3O_3$ (MH+): calcd, 470.2819; found, 470.2859.

EXAMPLE 15

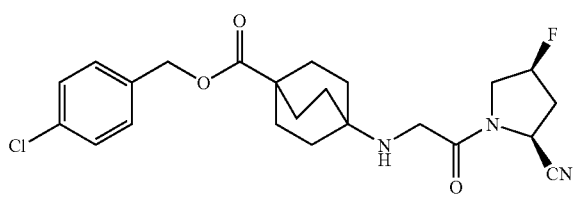

Synthesis of (2S,4S)-1-[[N-[4-(4-chlorobenzyl)oxycarbonyl bicyclo[2.2.2]oct-1-yl]amino]acetyl]-4-fluoropyrrolidine-2-carbonitrile In a similar manner to Example 8, (2S,4S)-1-[[N-(4-carboxybicyclo[2.2.2]oct-1-yl)amino]acetyl]-4-fluoropyrrolidine-2-carbonitrile (30.0 mg) and 4-chlorobenzyl bromide (21.0 mg) were used to obtain (2S,4S)-1-[[N-[4-(4-chlorobenzyl)oxycarbonylbicyclo[2.2.2]oct-1-yl]amino]acetyl]-4-fluoropyrrolidine-2-carbonitrile (25.5 mg).

MS (FAB+) m/z: 448 (MH+).

HRMS (FAB+) for $C_{23}H_{28}ClFN_3O_3$ (MH+): calcd, 448.1803; found, 448.1794.

EXAMPLE 16

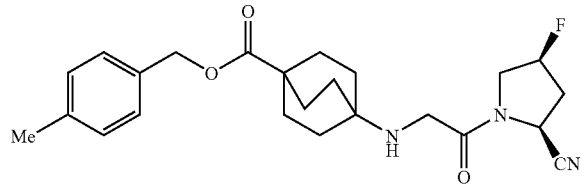

Synthesis of (2S,4S)-4-fluoro-1-[[N-[4-(4-methylbenzyl)oxycarbonylbicyclo[2.2.2]oct-1-yl]amino]acetyl]pyrrolidine-2-carbonitrile In a similar manner to Example 8, (2S,4S)-1-[[N-(4-carboxybicyclo[2.2.2]oct-1-yl)amino]acetyl]-4-fluoropyrrolidine-2-carbonitrile (30.0 mg) and 4-methylbenzyl bromide (18.9 mg) were used to obtain (2S,4S)-4-fluoro-1-[[N-[4-(4-methylbenzyl)oxycarbonylbicyclo[2.2.2]oct-1-yl]amino]acetyl]pyrrolidine-2-carbonitrile (9.2 mg).

MS (FAB+) m/z: 428 (MH+).

HRMS (FAB+) for $C_{24}H_{31}FN_3O_3$ (MH+): calcd, 428.2349; found, 428.2382.

EXAMPLE 17

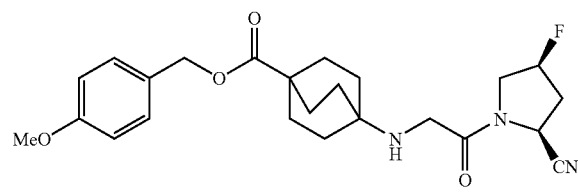

Synthesis of (2S,4S)-4-fluoro-1-[[N-[4-(4-methoxybenzyl)oxycarbonylbicyclo[2.2.2]oct-1-yl]amino]acetyl]pyrrolidine-2-carbonitrile In a similar manner to Example 8, (2S,4S)-1-[[N-(4-carboxybicyclo[2.2.2]oct-1-yl)amino]acetyl]-4-fluoropyrrolidine-2-carbonitrile (30.0 mg) and 4-methoxybenzyl chloride (16.0 mg) were used to obtain (2S,4S)-4-fluoro-1-[[N-[4-(4-methoxybenzyl)oxycarbonylbicyclo[2.2.2]oct-1-yl]amino]acetyl]pyrrolidine-2-carbonitrile (29.8 mg).

MS (FAB$^+$) m/z: 444 (MH$^+$).

HRMS (FAB$^+$) for C$_{24}$H$_{31}$FN$_3$O$_4$ (MH$^+$): calcd, 444.2299; found, 444.2269.

EXAMPLE 18

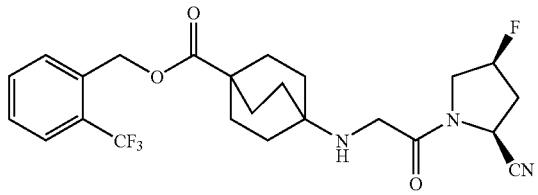

Synthesis of (2S,4S)-4-fluoro-1-[[N-[4-(2-trifluoromethylbenzyl)oxycarbonylbicyclo[2.2.2]oct-1-yl]amino]acetyl]pyrrolidine-2-carbonitrile In a similar manner to Example 8, (2S,4S)-1-[[N-(4-carboxybicyclo[2.2.2]oct-1-yl)amino]acetyl]-4-fluoropyrrolidine-2-carbonitrile (30.0 mg) and 2-trifluoromethylbenzyl bromide (25.4 mg) were used to obtain (2S,4S)-4-fluoro-1-[[N-[4-(2-trifluoromethylbenzyl)oxycarbonyl bicyclo[2.2.2]oct-1-yl]amino]acetyl]pyrrolidine-2-carbonitrile (39.9 mg).

MS (EI$^+$) m/z: 481 (M$^+$).

HRMS (EI$^+$) for C$_{24}$H$_{27}$F$_4$N$_3$O$_3$ (M$^+$): calcd, 481.1989; found, 481.1944.

EXAMPLE 19

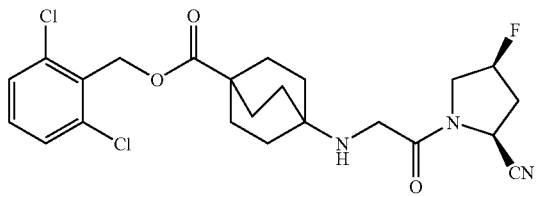

Synthesis of (2S,4S)-1-[[N-[4-(2,6-dichlorobenzyl)oxycarbonyl bicyclo[2.2.2]oct-1-yl]amino]acetyl]-4-fluoropyrrolidine-2-carbonitrile In a similar manner to Example 8, (2S,4S)-1-[[N-(4-carboxybicyclo[2.2.2]oct-1-yl)amino]acetyl]-4-fluoropyrrolidine-2-carbonitrile (30.0 mg) and 2,6-dichlorobenzyl bromide (24.5 mg) were used to obtain (2S,4S)-1-[[N-[4-(2,6-dichlorobenzyl)oxycarbonylbicyclo[2.2.2]oct-1-yl]amino]acetyl]-4-fluoropyrrolidine-2-carbonitrile (40.0 mg).

MS (EI$^+$) m/z: 481 (M$^+$).

HRMS (EI$^+$) for C$_{23}$H$_{26}$Cl$_2$FN$_3$O$_3$ (M$^+$): calcd, 481.1335; found, 481.1366.

EXAMPLE 20

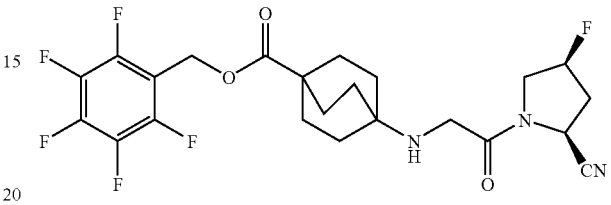

Synthesis of (2S,4S)-4-fluoro-1-[[N-[4-(2,3,4,5,6-pentafluorobenzyl)oxycarbonylbicyclo[2.2.2]oct-1-yl]amino]acetyl]pyrrolidine-2-carbonitrile In a similar manner to Example 8, (2S,4S)-1-[[N-(4-carboxybicyclo[2.2.2]oct-1-yl)amino]acetyl]-4-fluoropyrrolidine-2-carbonitrile (30.0 mg) and 2,3,4,5,6-pentafluorobenzyl bromide (26.6 mg) were used to obtain (2S,4S)-4-fluoro-1-[[N-[4-(2,3,4,5,6-pentafluorobenzyl)oxycarbonylbicyclo[2.2.2]oct-1-yl]amino]acetyl]pyrrolidine-2-carbonitrile (41.9 mg).

MS (EI$^+$) m/z: 503 (M$^+$).

HRMS (EI$^+$) for C$_{23}$H$_{23}$F$_6$N$_3$O$_3$ (M$^+$): calcd, 503.1644; found, 503.1681.

EXAMPLE 21

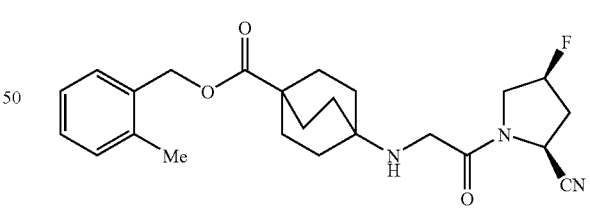

Synthesis of (2S,4S)-4-fluoro-1-[[N-[4-(2-methylbenzyl)oxycarbonylbicyclo[2.2.2]oct-1-yl]amino]acetyl]pyrrolidine-2-carbonitrile In a similar manner to Example 8, (2S,4S)-1-[[N-(4-carboxybicyclo[2.2.2]oct-1-yl)amino]acetyl]-4-fluoropyrrolidine-2-carbonitrile (30.0 mg) and 2-methylbenzyl bromide (18.9 mg) were used to obtain (2S,4S)-4-fluoro-1-[[N-[4-(2-methylbenzyl)oxycarbonylbicyclo[2.2.2]oct-1-yl]amino]acetyl]pyrrolidine-2-carbonitrile (34.1 mg).

MS (EI+) m/z: 427 (M+).

HRMS (EI+) for $C_{24}H_{30}FN_3O_3$ (M+): calcd, 427.2271; found, 427.2312.

EXAMPLE 22

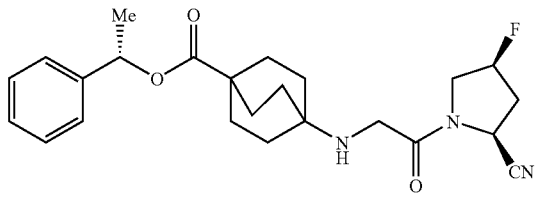

Synthesis of (2S,4S,1'S)-1-[[N-(1-phenylethyloxy-carbonyl bicyclo[2.2.2]oct-1-yl)amino]acetyl]-4-fluoropyrrolidine-2-carbonitrile (2S,4S)-1-[[N-(4-Carboxybicyclo[2.2.2]oct-1-yl)amino]acetyl]-4-fluoropyrrolidine-2-carbonitrile (50.0 mg), 1-hydroxybenzotriazole (26.0 mg) 1-(3-dimethylaminopropyl)-3-ethylcarbodiimide hydrochloride (32.5 mg), and (1S)-phenethyl alcohol (0.094 mL) were dissolved in N,N-dimethylformamide (0.9 mL). The mixture was stirred at room temperature for 22 days and was subsequently concentrated under reduced pressure.

The resulting residue was purified by thin layer chromatography (eluant: dichloromethane:methanol=10:1) to give (2S,4S,1'S)-1-[[N-(1-phenylethyloxycarbonyl bicyclo[2.2.2]oct-1-yl)amino]acetyl]-4-fluoropyrrolidine-2-carbonitrile (4.6 mg).

MS (FAB+) m/z: 428 (MH+).

HRMS (FAB+) for $C_{24}H_{31}FN_3O_3$ (MH+): calcd, 428.2349; found, 428.2369.

EXAMPLE 23

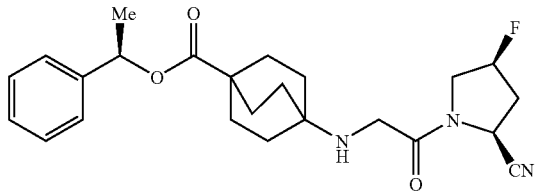

Synthesis of (2S,4S,1'R)-1-[[N-(1-phenylethyloxy-carbonyl bicyclo[2.2.2]oct-1-yl)amino]acetyl]-4-fluoropyrrolidine-2-carbonitrile In a similar manner to Example 22, (2S,4S)-1-[[N-(4-carboxybicyclo[2.2.2]oct-1-yl)amino]acetyl]-4-fluoropyrrolidine-2-carbonitrile (50.0 mg), 1-hydroxybenzotriazole (26.0 mg), and (1R)-phenethyl alcohol (0.094 mL) were used to obtain (2S,4S,1'R)-1-[[N-(1-phenylethyloxycarbonylbicyclo[2.2.2]oct-1-yl)amino]acetyl]-4-fluoropyrrolidine-2-carbonitrile (3.6 mg).

MS (FAB+) m/z: 428 (MH+).

HRMS (FAB+) for $C_{24}H_{31}FN_3O_3$ (MH+): calcd, 428.2349; found, 428.2342.

EXAMPLE 24

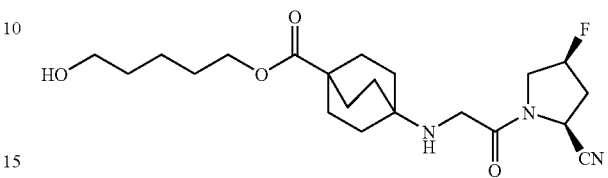

Synthesis of (2S,4S)-4-fluoro-1-[[N-(5-hydroxypentyloxycarbonylbicyclo[2.2.2]oct-1-yl)amino]acetyl]pyrrolidine-2-carbonitrile (2S,4S)-1-[[N-(4-Carboxybicyclo[2.2.2]oct-1-yl)amino]acetyl]-4-fluoropyrrolidine-2-carbonitrile (50.0 mg), 5-bromo-1-pentanol (18.7 μL), potassium carbonate (23.5 mg), and N,N-dimethylformamide (1.5 mL) were mixed together. The mixture was stirred at room temperature for 4 hours. The insoluble materials in the mixture was filtered and the filtrate was concentrated under reduced pressure. The resulting residue was purified by a silica gel column (eluant: chloroform:methanol=10:1) to give (2S,4S)-4-fluoro-1-[[N-(5-hydroxypentyloxycarbonylbicyclo[2.2.2]oct-1-yl)amino]acetyl]pyrrolidine-2-carbonitrile (32.4 mg).

MS (FAB+) m/z: 410 (MH+).

HRMS (FAB+) for $C_{21}H_{33}FN_3O_4$ (MH+): calcd, 410.2455; found, 410.2420.

TEST EXAMPLE 1

Test for the Ability of the Compounds of the Invention to Inhibit of Dipeptidylpeptidase IV Activity The concentration of free 7-amino-4-methyl-coumarin (AMC) generated by hydrolysis of H-Gly-Pro-AMC.HBr substrate by plasma dipeptidylpeptidase IV was determined by fluorometry.

Method

A 20 μL of buffer (25 mmol/L hepes, 140 mmol/L sodium chloride, 1% bovine serum albumin, 80 mmol/L magnesium chloride hexahydrate, pH 7.4) containing each compound was added to 20 μL of plasma diluted 8-fold with saline in a well of a 96-well flat bottom plate. The plate was left at room temperature for 5 minutes and 10 μL of 0.1 mmol/L H-Gly-Pro-AMC.HBr solution was added to each well to initiate the reaction. The plate was left in a dark environment at room temperature for 20 minutes, at which point 20 μL 25% acetic acid was added to terminate the reaction. Using a fluorescent plate reader, the free AMC concentration was determined by exciting the samples at 355 nm and measuring the fluorescence intensity at 460 nm. Using Prism 3.02 (GraphPad Software), the results were analyzed to determine the 50% inhibitory concentration (IC50). The results are shown in Table 1.

TABLE 1

In vitro dipeptidylpeptidase IV inhibitory activity

| Test compound | IC50 (nmol/L) |
| --- | --- |
| Example 1 | 0.25 |
| Example 9 | 0.48 |
| Example 10 | 0.23 |
| Example 11 | 0.13 |
| Compound A | 3.3 |

Compound A: (2S)-1-[[(3-hydroxy-1-adamantyl)amino]acetyl]-2-cyanopyrrolidine (LAF-237)

TEST EXAMPLE 2

Test for the Inhibition of Dipeptidylpeptidase IV Activity in Mice by Oral Administration of the Compounds of the Invention Each compound was suspended in 0.3% sodium carboxymethylcellulose to a concentration of 0.1 mg/mL. The preparation was orally administered to 8-week old male ICR mice (Charles River Laboratories Japan) at a dose of 10 mL/kg. Using an EDTA 2K-treated capillary tube, blood samples were collected from the tail vein before administration and 30 minutes after administration. The blood samples were centrifuged at 6000 rpm for 2 minutes to separate plasma. The enzymatic activity was determined using the same procedure as in Test Example 1. The inhibition was determined from the decrease in the enzymatic activity from the initial activity (% inhibition={(activity before administration−activity after administration)/(activity before administration)}×100). The results are shown in Table 2.

TABLE 2

Inhibition of plasma dipeptidylpeptidase IV activity by oral administration

| Test compound | % inhibition |
| --- | --- |
| Example 1 | 100 |
| Example 9 | 94 |
| Example 11 | 93 |
| Compound A | 81 |

Compound A: (2S)-1-[[(3-hydroxy-1-adamantyl)amino]acetyl]-2-cyanopyrrolidine (LAF-237)

TEST EXAMPLE 3

Oral Glucose Tolerance Test in Mice

The compound of the present invention of Example 1 was suspended in 0.3% sodium carboxymethylcellulose (CMC-Na, Sigma). Seven weeks old male ICR mice (Charles River Laboratories Japan) were acclimatized for 1 week. During the acclimatization period, the animals were allowed to freely consume standard feed (CE-2, Clea Japan) and water. The ICR mice reaching 8-weeks old were fasted for 16 hours. Subsequently, the animals were orally administered 0.3% CMC-Na (10 mL/kg) or Compound 1 (1 mg/kg, 10 mL/kg) and were immediately administered a glucose solution orally at a dose of 5 g/kg. Using an EDTA 2K-treated capillary tube, blood samples were collected from the tail vein before administration of glucose solution and 15, 30, 60, and 120 minutes after administration. The blood glucose level was determined using glucose B-test Wako (Wako Pure Chemical Industries). The results were shown in means±standard errors. Statistical analysis was performed using t-test with a significant level of less than 5%. The results are shown in FIG. 1.

TEST EXAMPLE 4

Test for the Efficacy of the Compounds of the Invention Against Drug-Induced Hypoleukocytosis The efficacy of the compounds of the present invention against drug-induced hypoleukocytosis was evaluated by conducting an experiment according to the method described by Okabe et al (Japanese Pharmacology and Therapeutics, Vol. 19, No. 6 (1991): p 55).

Eight weeks old male ICR mice (Charles River Laboratories Japan) were intraperitoneally administered a single dose of cyclophosphamide (200 mg/kg) on Day 0, Starting from the following day, control group was given saline and test group was orally administered the compound of the present invention (1 to 200 mg/kg) once or twice a day over a five day period. Blood samples were collected 2, 4, 6, and 8 days after the beginning of the test and the white blood cell count was monitored over time. The white blood cell count of the test group at a given time was compared with the white blood cell count before administration of cyclophosphamide to evaluate the efficacy of the compound of the present invention against the drug-induced hypoleukocytosis. The results indicate that the decrease in the white blood cell count was significantly suppressed in the group administered the compound of the present invention as compared to control group.

TEST EXAMPLE 5

Test for the Ability of the Compounds of the Invention to Increase the Blood G-CSF Level Seven weeks old male ICR mice (Charles River Laboratories Japan) were used. Control group was given saline and test group was orally administered the compound of the present invention (1 to 200 mg/kg) once or twice a day over a five day period. Mice were anesthetized on the day following the cessation of administration and blood samples were collected. Plasma G-CSF level was determined using mouse G-CSF ELISA kit (R&D SYSTEM). The results indicate that the plasma G-CSF level was significantly increased in the group administered the compound of the present invention as compared to control group.

INDUSTRIAL APPLICABILITY

As set forth, the compounds of the present invention are novel bicycloester derivatives and pharmaceutically acceptable salts thereof that have high DPP-IV inhibitory activity. Pharmaceutical compositions that contain the compound of the present invention as an active ingredient are useful in the prevention and/or treatment of diabetes and associated diabetic complications, as well as in the prevention and/or treatment of other diseases that involve DPP-IV.

The invention claimed is:

1. A bicycloester derivative represented by the following formula (1):

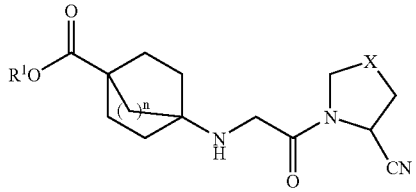

wherein $R^1$ is a substituted or unsubstituted $C_1$ to $C_6$ alkyl group, substituted or unsubstituted arylmethyl group, or substituted or unsubstituted arylethyl group; X is $CH_2$, CHF or $CF_2$; and n is 1 or 2, or a pharmaceutically acceptable salt thereof.

2. The bicycloester derivative according to claim 1, or a pharmaceutically acceptable salt thereof, wherein in formula (1), X is $CH_2$.

3. The bicycloester derivative according to claim 1, or a pharmaceutically acceptable salt thereof, wherein in formula (1), X is CHF.

4. The bicycloester derivative according to claim 1, or a pharmaceutically acceptable salt thereof, wherein in formula (1), n is 1.

5. The bicycloester derivative according to claim 1, or a pharmaceutically acceptable salt thereof, wherein in formula (1), n is 2.

6. The bicycloester derivative according to claim 1, or a pharmaceutically acceptable salt thereof, wherein in formula (1), $R^1$ is a $C_1$ to $C_6$ alkyl group that may have 1 to 5 substituents selected from the group consisting of halogen atom, hydroxyl group, cyano group, $C_1$ to $C_6$ alkoxy group, substituted or unsubstituted aryloxy group, $C_1$ to $C_6$ alkylcarbonyl group, $C_1$ to $C_6$ alkoxycarbonyl group, $C_1$ to $C_6$ alkylthio group, amino group, mono- or di-substituted $C_1$ to $C_6$ alkylamino group, 4- to 9-membered cyclic amino group that may contain 1 to 3 heteroatoms, formylamino group, $C_1$ to $C_6$ alkylcarbonylamino group, $C_1$ to $C_6$ alkoxycarbonylamino group, $C_1$ to $C_6$ alkylsulfonylamino group and substituted or unsubstituted arylsulfonylamino group.

7. The bicycloester derivative according to claim 1, or a pharmaceutically acceptable salt thereof, wherein in formula (1), $R^1$ is an alkyl group selected from the group consisting of methyl group, ethyl group, propyl group, 1-methylethyl group, 1-methylpropyl group, 2-methylpropyl group, 1-ethyipropyl group, 2-ethyipropyl group, butyl group and hexyl group.

8. The bicycloester derivative according to claim 1, or a pharmaceutically acceptable salt thereof, wherein the compound represented by formula (1) is a compound selected from the group consisting of (2S, 4S)-1-[[N-(4-ethoxycarbonylbicyclo [2.2.2]oct-1-yl)amino]acetyl]-4-fluoropyrrolidine-2-carbonitrile, (2S)-1-]]N-4-ethoxycarbonylbicyclo [2.2.2]oct-1-yl) amino]acetyl]pyrrolidine-2-carbonitrile, (2S ,4S)-1-]]N-(4-ethoxycarbonylbicyclo [2.2.1]hept-1-yl) amino]acetyl]-4-fluoropyrrolidine-2-carbonitrile, (2S)-1-[[N-(4-ethoxycarbonylbicyclo [2.2.1]hept-1-yl)amino] acetyl]pyrrolidine-2-carbonitrile, (2S ,4S)-1-[[N-(4-benzyloxycarbonylbicyclo [2.2.2]oct-1-yl)amino]acetyl]-4-fluoropyrrolidine-2-carbonitrile, (2S ,4S)-4-fluoro- 1-[[N-(4-(4-trifluoromethyl)benzyloxycarbonylbicyclo [2.2.2]oct-1-yl)amino]acetyl]pyrrolidine-2-carbonitrile, (2S ,4S)-4-fluoro-1-[[N-(4-isobutyloxycarbonylbicyclo [2.2.2]oct-1-yl) amino]acetyl]pyrrolidine-2-carbonitrile, and (2S ,4S)-4-fluoro-1-[[N-(4-isopropyloxycarbonylbicyclo [2.2.2] oct-1 -yl)amino]acetyl]pyrrolidine-2-carbonitrile.

* * * * *